United States Patent
Chu et al.

(10) Patent No.: US 9,233,788 B2
(45) Date of Patent: Jan. 12, 2016

(54) BIOSENSOR DESICCANT SYSTEM HAVING ENHANCED MEASUREMENT PERFORMANCE

(75) Inventors: Amy H. Chu, Elkhart, IN (US); Mary Ellen Warchal-Windham, Osceola, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 589 days.

(21) Appl. No.: 13/553,203

(22) Filed: Jul. 19, 2012

(65) Prior Publication Data

US 2013/0186755 A1 Jul. 25, 2013

Related U.S. Application Data

(63) Continuation-in-part of application No. PCT/US2011/022258, filed on Jan. 24, 2011.

(60) Provisional application No. 61/297,515, filed on Jan. 22, 2010, provisional application No. 61/510,687, filed on Jul. 22, 2011.

(51) Int. Cl.
*G01N 27/327* (2006.01)
*B65D 81/26* (2006.01)
*C12Q 1/00* (2006.01)
(Continued)

(52) U.S. Cl.
CPC .............. *B65D 81/266* (2013.01); *B65B 55/00* (2013.01); *C12Q 1/005* (2013.01); *G01N 33/48778* (2013.01); *G01N 27/3272* (2013.01)

(58) Field of Classification Search
CPC .......... G01N 27/3272; G01N 27/3273; G01N 33/48778
See application file for complete search history.

(56) References Cited

U.S. PATENT DOCUMENTS 5,120,420 A * 6/1992 Nankai et al. ............ 204/403.11
5,393,615 A   2/1995 Corey et al.
(Continued)

FOREIGN PATENT DOCUMENTS

| EP | 1785483 | 5/2010 |
|---|---|---|
| EP | 2549270 | 1/2013 |
| WO | 9109139 | 6/1991 |

OTHER PUBLICATIONS

The product description for DesiMax SLF® from the Multisorb Technologies, Inc. website downloaded on Dec. 11, 2014.*
(Continued)

*Primary Examiner* — Alexander Noguerola
(74) *Attorney, Agent, or Firm* — Nixon Peabody LLP

(57) ABSTRACT

A biosensor system for determining the concentration of an analyte in a sample includes a plurality of test sensors, and includes a container including a desiccant and the plurality of test sensors, sealed in the container. When the container is stored for two weeks at a temperature of 50° C., and each test sensor is subsequently removed from the container, connected through the at least two conductors to a measurement device and then contacted with one of a plurality of samples including an analyte, where the plurality of samples has analyte concentrations that span the range of 50 mg/dL-600 mg/dL, and the analyte concentration in each sample is determined by the test sensor and the measuring device, the bias of each determined analyte concentration may be within ±10 mg/dL or ±10%, and the coefficient of variation of the determined analyte concentrations may be at most 2.5%.

20 Claims, 7 Drawing Sheets

(51) Int. Cl.
 B65B 55/00 (2006.01)
 G01N 33/487 (2006.01)

(56) References Cited

U.S. PATENT DOCUMENTS

| | | | |
|---|---|---|---|
| 5,498,542 | A | 3/1996 | Corey et al. |
| 5,520,786 | A | 5/1996 | Bloczynski et al. |
| 6,187,269 | B1 * | 2/2001 | Lancesseur et al. .......... 422/401 |
| 6,488,828 | B1 * | 12/2002 | Bhullar et al. .......... 204/403.01 |
| 7,862,696 | B2 | 1/2011 | Wu et al. |
| 8,147,674 | B2 | 4/2012 | Wu |
| 8,231,548 | B2 | 7/2012 | Hoenes |
| 8,252,523 | B2 | 8/2012 | Zhu |
| 2002/0179442 | A1 | 12/2002 | Miyazaki et al. |
| 2003/0185708 | A1 * | 10/2003 | Otake ............................. 422/61 |
| 2003/0200644 | A1 | 10/2003 | Matzinger |
| 2004/0040839 | A1 * | 3/2004 | Yagi .......................... 204/403.01 |
| 2005/0247573 | A1 | 11/2005 | Nakamura et al. |
| 2008/0121523 | A1 | 5/2008 | Chuang et al. |
| 2008/0173552 | A1 | 7/2008 | Wu et al. |
| 2009/0177406 | A1 | 7/2009 | Wu |
| 2011/0297540 | A1 | 12/2011 | Chu et al. |
| 2011/0297554 | A1 | 12/2011 | Wu et al. |

OTHER PUBLICATIONS

The "Desiccant Moisture Adsorption" graph and the "Moisture pickup 0-10% rH Detail at low levels" graph from Brownell Ltd. downloaded Dec. 11, 2014, but dated "Issue Sep. 1, 1997".*

"Influence of Temperature on Relative Humidity within Confined Spaces With and Without a Desiccant," United States Department of Agriculture Forest Service, No. R1498, Jul. 1953 (information reviewed and reaffirmed 1959).*

International Searching Authority, "International Search Report and Written Opinion for PCT/US2011/022258", Oct. 11, 2011, Publisher: Korean Intellectual Property Office.

* cited by examiner

BIOSENSOR DESICCANT SYSTEM HAVING ENHANCED MEASUREMENT PERFORMANCE

REFERENCE TO RELATED APPLICATIONS

This application claims the benefit of U.S. Provisional Application No. 61/510,687 entitled "Biosensor Desiccant System Having Enhanced Measurement Performance" filed Jul. 22, 2011, and is a continuation-in-part of PCT Application No. PCT/US2011/022258 entitled "Accuracy Improving Desiccants" filed Jan. 24, 2011, which claims the benefit of U.S. Provisional Application No. 61/297,515 entitled "Accuracy Improving Desiccants" filed Jan. 22, 2010, which are incorporated by reference in their entirety.

BACKGROUND

Biosensors provide an analysis of a biological fluid, such as whole blood, serum, plasma, urine, saliva, interstitial, or intracellular fluid. Typically, biosensors have a measurement device that analyzes a sample residing in a test sensor. The sample usually is in liquid form and may be a biological fluid or a derivative of a biological fluid, such as an extract, a dilution, a filtrate, or a reconstituted precipitate. The analysis performed by the biosensor determines the presence and/or concentration of one or more analytes in the biological fluid. Examples of analytes include alcohol, glucose, uric acid, lactate, cholesterol, bilirubin, free fatty acids, triglycerides, proteins, ketones, phenylalanine, or enzymes. The analysis may be useful in the diagnosis and treatment of physiological abnormalities. For example, a diabetic individual may use a biosensor to determine the glucose level in whole blood, and this information may be used in adjusting the individual's diet and/or medication.

Biosensors may be designed to analyze one or more analytes and may use different sample volumes. Some biosensors may analyze a single drop of whole blood, such as from 0.25-15 microliters (µL) in volume. Biosensors may be implemented using bench-top, portable, and like measurement devices. Portable measurement devices may be hand-held and allow for the identification and/or quantification of one or more analytes in a sample. Examples of portable measurement devices include the BREEZE® and CONTOUR® meters of Bayer HealthCare in Tarrytown, N.Y., while examples of bench-top measurement devices include the Electrochemical Workstation available from CH Instruments in Austin, Tex.

In electrochemical biosensors, the analyte concentration is determined from an electrical signal generated by an oxidation/reduction or redox reaction of the analyte, or of a species responsive to the analyte, when an input signal is applied to the sample. The input signal may be applied as a single electrical pulse or in multiple pulses, sequences, or cycles. A redox substance, such as a mediator, an enzyme or similar species, may be added to the sample to enhance the electron transfer from a first species to a second species during the redox reaction. The redox substance(s) may react with a single analyte, thus providing specificity to a portion of the generated output signal.

Electrochemical biosensors usually include a measurement device having electrical contacts that connect with electrical conductors in the test sensor. The test sensor may be adapted for use outside, inside, or partially inside a living organism. When used outside a living organism, a sample of the biological fluid is introduced into a sample reservoir in the test sensor. The test sensor may be placed in the measurement device before, after, or during the introduction of the sample for analysis. When inside or partially inside a living organism, the test sensor may be continually immersed in the sample, or the sample may be introduced intermittently to the test sensor. The test sensor may include a reservoir that partially isolates a volume of the sample, or the test sensor may be open to the sample. Similarly, the sample may continuously flow through the test sensor or be interrupted for analysis.

The test sensor may be formed by disposing or printing electrodes on an insulating base, such as by disposing one or more reagent compositions on one or more of the conductors. More than one of the conductors may be coated by the same reagent composition, such as when the working and counter electrodes are coated by the same composition. Multiple techniques known to those of ordinary skill in the art may be used to dispose the reagent composition on the test sensor. The reagent composition may be disposed on the conductors as a reagent fluid and then dried. When the sample is introduced to the test sensor, the reagent composition begins to rehydrate.

The reagent compositions disposed on each conductor may be the same or different. Thus, the reagent composition of the working electrode may contain an enzyme, a mediator and a binder, while the reagent composition of the counter electrode may contain only a mediator, which could be the same as or different from the mediator of the working electrode, and a binder. The reagent composition may include an ionizing agent for facilitating the oxidation or reduction of the analyte, such as an oxidoreductase enzyme, as well as any mediators or other substances that assist in transferring electrons between the analyte and the working electrode.

One or more components of a reagent composition may undergo a chemical transformation prior to use of the test sensor. In particular, it is believed that the oxidation state of the mediator may change over time under certain conditions. Mediators such as ferricyanide and organic quinones and hydroquinones may undergo reduction in the presence of water. The presence of reduced mediator in the reagent composition can cause an increase in background current of the sensor, leading to inaccurate and imprecise assay results, particularly for samples with low analyte concentration.

Typically, undesirable and/or premature chemical transformations in the reagent composition are inhibited by storing the test sensor in proximity to a desiccant. Desiccants typically are used in test sensor primary packaging, such as bottles or foil pouches, to prevent degradation of the reagent composition so as to maintain the desired shelf life of the test sensor. Conventional desiccants for test sensor storage systems can quickly adsorb moisture that may leak into the package containing the test sensor. Examples of desiccants used to protect test sensors include molecular sieves, such as those containing porous crystalline alumino-silicates, which quickly adsorb moisture even in low humidity environments.

A drawback to the protection of test sensors with a desiccant is that one or more components of the reagent composition may require a minimum level of moisture to retain their function in the composition. For example, the FAD dependent Glucose Dehydrogenase enzyme (FAD-GDH) is believed to require some residual moisture to maintain its native active configuration. Depletion of moisture from the reagent composition below a minimum level could lead to enzyme conformational change and inactivation of at least a portion of the FAD-GDH. Depletion of moisture from the reagent composition may result in inactivation of at least a portion of one or more other components of the reagent composition.

Loss of activity of an enzyme in the reagent composition due to excessive desiccation of the test sensor typically is addressed either by including excess amounts of enzyme in the reagent composition or by adding a substance to the reagent composition that is believed to stabilize the enzyme. Examples of substances that may stabilize the enzyme in a test sensor reagent composition include sugars such as trehalose or sucrose, and sugar alcohols such as mannitol, maltitol or sorbitol. These substances may be used in a lyophilization process to preserve enzyme activity. See, for example EP 1 785 483 A1. High loadings of the enzyme or of other substances such as stabilizers in the reagent composition can present other difficulties, however. Since the enzyme component typically is expensive, it is not desirable to increase the enzyme loading beyond the level needed for the assay. In addition, the enzyme or stabilizers can slow down the rehydration of the reagent composition by the sample, resulting in longer assay times, especially at lower temperatures. Excess enzyme in the test sensor, beyond that required for interaction with the analyte and/or an excess of other ingredients in the reagent composition such as the mediator, also may reduce the accuracy of the sensor.

Accordingly, there is an ongoing need for improved biosensor systems, especially those that may provide increasingly accurate and/or precise determination of the concentration of the analyte in the sample, and/or that may provide increasingly shorter analysis times. Moreover, there is a need for improved biosensor systems that have an increased shelf life over a wider range of storage conditions, while supplying the desired accuracy, precision and/or analysis time. The systems, devices, and methods of the present invention overcome at least one of the disadvantages associated with conventional biosensor systems.

SUMMARY

In one aspect, the invention provides a biosensor system for determining the concentration of an analyte in a sample that includes a plurality of test sensors. Each test sensor includes at least two conductors, where one of the conductors is a working electrode, and further includes a reagent composition disposed on or near the working electrode. The biosensor system further includes a container including a desiccant and the plurality of test sensors, sealed in the container. When the container is stored for two weeks at a temperature of 50° C., and each test sensor is subsequently removed from the container, connected through the at least two conductors to a measurement device and then contacted with one of a plurality of samples including an analyte, where the plurality of samples has analyte concentrations that span the range of 50 mg/dL-600 mg/dL, and the analyte concentration in each sample is determined by the test sensor and the measuring device, the bias of each determined analyte concentration less than 100 mg/dL is within ±10 mg/dL, and the bias of each determined analyte concentration of at least 100 mg/dL is within ±10%.

In another aspect, the invention provides a biosensor system for determining the concentration of an analyte in a sample that includes a plurality of test sensors. Each test sensor includes at least two conductors, where one of the conductors is a working electrode, and further includes a reagent composition disposed on or near the working electrode, where the reagent composition includes a redox enzyme having an activity. The biosensor system further includes a container including a desiccant and the plurality of test sensors, sealed in the container. When the container is stored for two weeks at a temperature of 50° C., and each test sensor is subsequently removed from the container, the reagent composition of each test sensor retains at least 75% of the activity of the redox enzyme.

In another aspect, the invention provides a biosensor system for determining the concentration of an analyte in a sample that includes a plurality of test sensors. Each test sensor includes at least two conductors, where one of the conductors is a working electrode, and further includes a reagent composition disposed on or near the working electrode. The biosensor system further includes a container including a desiccant and the plurality of test sensors, sealed in the container. When the container is stored for two weeks at a temperature of 50° C., and each test sensor is subsequently removed from the container, connected through the at least two conductors to a measurement device and then contacted with one of a plurality of samples including an analyte, where the plurality of samples has analyte concentrations that span the range of 50 mg/dL-600 mg/dL, and the analyte concentration in each sample is determined by the test sensor and the measuring device, the coefficient of variation of the determined analyte concentrations is at most 2.5%.

In another aspect, the invention provides a method of increasing the measurement performance of a test sensor that includes sealing the test sensor in a container including a desiccant. The test sensor includes at least two conductors, one of which is a working electrode, and a reagent composition disposed on or near the working electrode. The desiccant adsorbs at most 15% of its weight in water when in contact with an environment of 10%-20% RH at 40° C.

In another aspect, the invention provides a biosensor system for determining the concentration of an analyte in a sample that includes a plurality of test sensors. Each test sensor includes at least two conductors, where one of the conductors is a working electrode, and further includes a reagent composition disposed on or near the working electrode. The biosensor system further includes a container including a desiccant and the plurality of test sensors, sealed in the container. The desiccant adsorbs at most 15% of its weight in water when in contact with an environment of 10%-20% RH at 40° C.

In another aspect, the invention provides a biosensor system for determining the concentration of an analyte in a sample that includes a plurality of test sensors. Each test sensor includes at least two conductors, where one of the conductors is a working electrode, and further includes a reagent composition disposed on or near the working electrode. The biosensor system further includes a container including a desiccant and the plurality of test sensors, sealed in the container. When the container is stored for two weeks at a temperature of 50° C., and each test sensor is subsequently removed from the container, connected through the at least two conductors to a measurement device and then contacted with one of a plurality of samples including an analyte, where the plurality of samples has analyte concentrations that span the range of 50 mg/dL-600 mg/dL, and the analyte concentration in each sample is determined by the test sensor and the measuring device, the bias of each determined analyte concentration less than 100 mg/dL is within ±10 mg/dL, the bias of each determined analyte concentration of at least 100 mg/dL is within ±10%, and the coefficient of variation of the determined analyte concentrations is at most 2.5%.

In another aspect, the invention provides a biosensor system for determining the concentration of an analyte in a sample that includes a plurality of test sensors. Each test sensor includes at least two conductors, where one of the conductors is a working electrode, and further includes a reagent composition, disposed on or near the working electrode. The reagent composition includes a redox enzyme having an activity, and is substantially free of a sugar or a sugar alcohol. The biosensor system further includes a container including the plurality of test sensors, sealed in the container. When the container is stored for two weeks at a temperature of 50° C., and each test sensor is subsequently removed from the container, the reagent composition of each test sensor retains at least 75% of the activity of the redox enzyme. The reagent composition may further include a mediator, and when the container is stored for two weeks at a temperature of 50° C., and each test sensor is subsequently removed from the container, connected through the at least two conductors to a measurement device and then contacted with one of a plurality of samples containing no analyte, the determined background currents may be within ±20% of the determined background currents of an identical plurality test sensors that had instead been stored for two weeks at −20° C.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 1A:
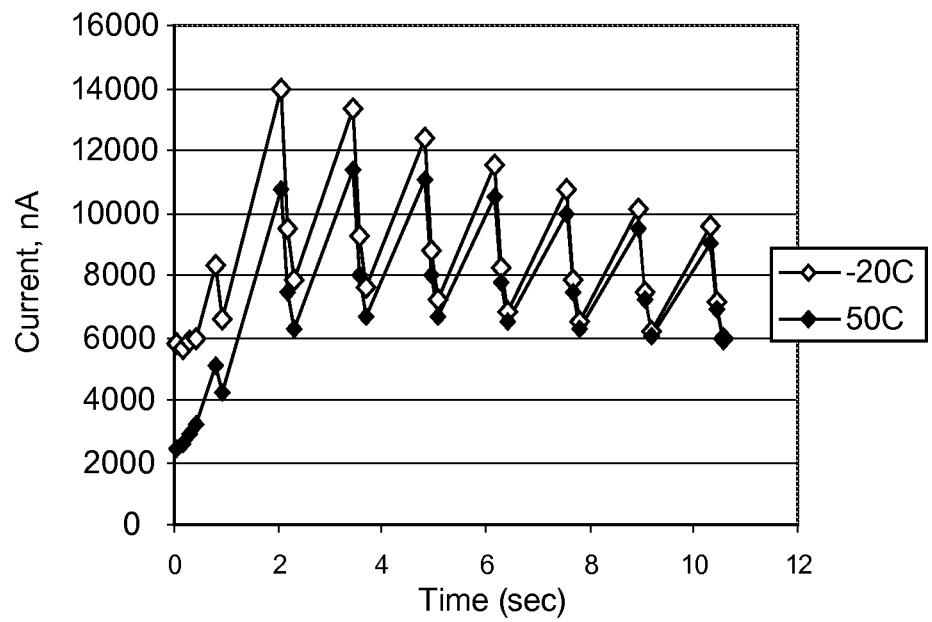
FIGS. 1A-1C represent the output signals from test sensors for whole blood samples having glucose concentrations of 400 milligrams per deciliter (mg/dL). The test sensors were sealed with molecular sieve desiccant (1A), silica gel desiccant (1B) or no desiccant (1C).

A biosensor system includes test sensors sealed in a container having a desiccant that retains a residual moisture level in the container. In low humidity environments, the desiccant does not quickly absorb moisture, which can allow the reagent compositions of the test sensors to maintain a moisture level conducive to maintaining an enzyme in its active configuration. Test sensors stored in a container including such a desiccant can provide determinations of analyte concentration that are more accurate and/or precise than those of comparable test sensors stored in a container including a conventional desiccant or no desiccant. Thus, test sensors of the biosensor system may provide consistently accurate assays with fast assay times, even when the test sensors are stored for long periods of time under non-optimal conditions.

A biosensor system includes a plurality of test sensors, each test sensor including at least two conductors, where one of the conductors is a working electrode, and a reagent composition disposed on or near the working electrode. The biosensor system further includes a container including a desiccant. The plurality of test sensors is sealed in the container.

The desiccant in the container of the biosensor system preferably adsorbs at most 15% of its weight in water when in contact with an environment of 10%-20% relative humidity (RH) at 40° C. More preferably the desiccant adsorbs at most 10% of its weight in water when in contact with an environment of 10%-20% RH at 40° C. More preferably the desiccant absorbs from 5%-10% of its weight in water when in contact with an environment of 10%-20% RH at 40° C.

An example of a desiccant that absorbs from 5%-10% of its weight in water when in contact with an environment of 10%-20% RH at 40° C. includes silica gel. Silica gels can adsorb moisture at a level roughly proportional to the relative humidity of the surrounding environment for RH values of 0% to approximately 60%. Thus, a sample of dry silica gel will absorb less water from a surrounding environment having a low relative humidity than an identical sample of dry silica gel would absorb from a surrounding environment having a higher relative humidity.

In contrast, the molecular sieve desiccants conventionally used in test sensor containers can adsorb large amounts of moisture quickly from environments having 10%-20% RH. Molecular sieves, such as those containing porous crystalline alumino-silicates, can adsorb more than 15% to 20% of their weight in water when in contact with an environment of 5% RH at 40° C., and then may adsorb minimal amounts of additional moisture as the relative humidity increases. Thus, a sample of dry molecular sieves will absorb the same amount of water from a surrounding environment having a low relative humidity as an identical sample of dry molecular sieves would absorb from a surrounding environment having a higher relative humidity, as long as the amount of absorbed water is less than the moisture capacity of the sample of dry molecular sieves.

An example of a desiccant that can absorb at most 15% of its weight in water when in contact with an environment of 10%-20% RH at 40° C. includes a composition of polymer-blended molecular sieves. The ability of a desiccant to absorb water may be lowered by blending the desiccant with a polymer. As the desiccant in the polymer is only partially exposed to the environment, moisture adsorption can occur at a rate that is slower than the adsorption rate of the pure desiccant. Another example of a desiccant that can absorb at most 15% of its weight in water when in contact with an environment of 10%-20% RH at 40° C. includes a blend of molecular sieves with silica gel. The selection of the types and relative amounts of molecular sieves and silica gel in the blend may allow for tailoring of the total moisture adsorbed by the blended composition at low relative humidity.

Figure 1B:
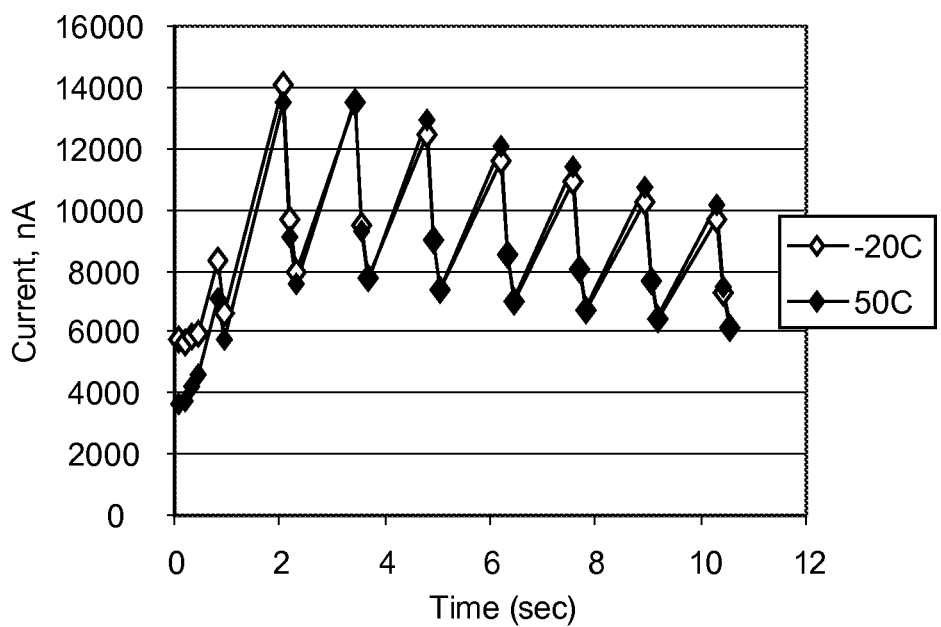
Figure 1C:
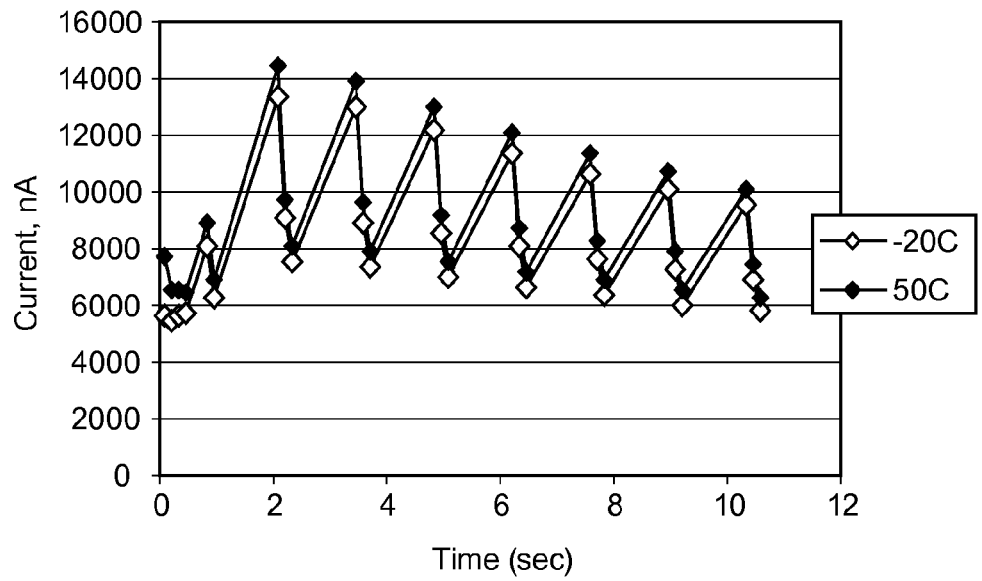

FIGS. 1A through 1C show test sensor output signals from whole blood samples having glucose concentrations of 400 milligrams per deciliter (mg/dL) and having hematocrit contents of 40%. The test sensors were sealed, in groups of 50 test sensors, in containers having either 22.5 mg per test sensor of the conventional desiccant "molecular sieve 13x" (FIG. 1A), 30 mg per test sensor of silica gel (FIG. 1B), or having no desiccant (FIG. 1C). The "molecular sieve 13x" desiccant included a sodium alumino-silicate having a "type X" crystal structure containing an effective pore opening of approximately 9 angstroms. For each type of desiccant, half of the containers were stored at 50° C. for two weeks, and half were stored at −20° C. for two weeks. The heat stress environment of two weeks at 50° C. is an accelerated stress condition typically used to assess the performance of a biosensor at the end of its shelf-life. After the storage period, test sensors were removed from their container, connected through their conductors to a measurement device, contacted with a whole blood sample including glucose as an analyte, and used to perform electrochemical assays of the whole blood samples.

The signal input to the test sensors by the measurement device was a gated amperometric pulse sequence, and one or more output current values were correlated with the analyte concentration of the sample, such as described in U.S. Patent Pub. 2008/0173552 to Wu et al., entitled "Gated Amperometry"; and in U.S. Patent Pub. 2009/0145779 to Wu, entitled "Rapid-Read Gated Amperometry". The disclosures of these patent applications regarding gated amperometric pulse sequences and the correlation of output current values with analyte concentrations are herein incorporated by reference.

Figure 1D:
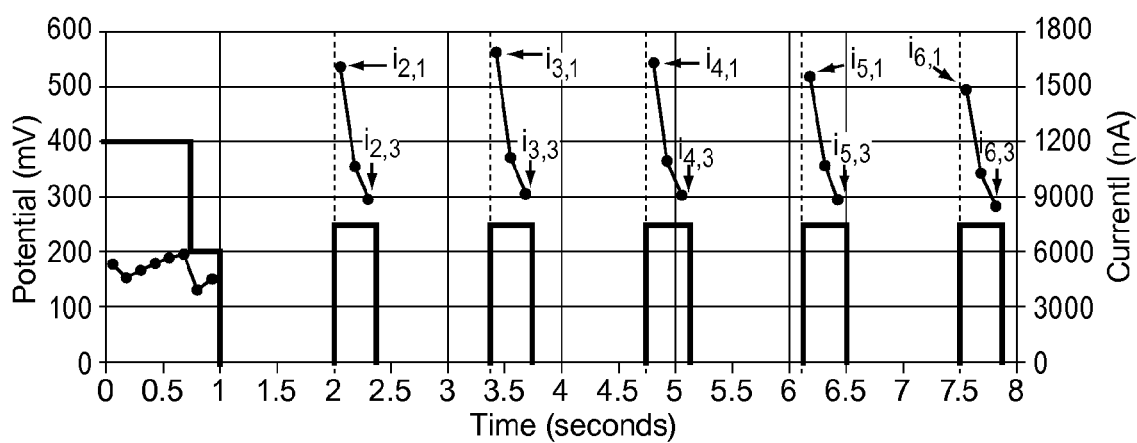
FIG. 1D depicts a gated pulse sequence where the input signal includes multiple pulses.

FIG. 1D depicts a gated pulse sequence where the input signal includes multiple pulses. The output signal current values resulting from the pulses are depicted above each pulse. The recorded intermediate signal current values are depicted as circles. Each of the i values is a current value of the output signal responsive to the input signal. The first number in the subscript of the i values denotes the pulse number, while the second number in the subscript denotes the order of the output signal as the current values were recorded. For example, $i_{2,3}$ denotes the third current value recorded for the second pulse.

The pulses used to generate the graphs of FIGS. 1A-1C included eight excitations separated by seven relaxations. The second through eighth excitations were about 0.4 second in duration, and the second through seventh relaxations were about 1 second in duration. Three output current values were recorded during the second through eighth excitations.

Output current values, such as those represented in FIGS. 1A-1D, may be related to analyte concentration in a sample through a correlation. A correlation of output current values with analyte concentrations of the sample may be prepared by plotting the output current at a particular time in the analysis against a known concentration of the analyte in a series of stock solutions containing the analyte. To correlate the output current values from the output signal with the analyte concentration of the sample, the initial current value from the excitation preferably is greater than those that follow in the decay. Preferably, the output current value or values correlated with the analyte concentration of the sample are taken from a decay including current data reflecting the maximum kinetic performance of the test sensor. The kinetics of the redox reaction underlying the output currents are affected by multiple factors. These factors may include the rate at which the reagent composition rehydrates, the rate at which the enzyme system reacts with the analyte, the rate at which the enzyme system transfers electrons to the mediator, and the rate at which the mediator transfers electrons to the electrode.

The maximum kinetic performance of a test sensor may be reached during an excitation of a gated amperometric pulse sequence when the initial current value of an excitation having decaying current values is greatest for the multiple excitations. Preferably, the maximum kinetic performance of a test sensor is reached when the last in time current value obtained for an excitation having decaying current values is the greatest last in time current value obtained for the multiple excitations. More preferably, the maximum kinetic performance of a test sensor is reached when the initial current value of an excitation having decaying current values is greatest for the multiple excitations, and the last in time current value obtained for the same excitation is the greatest last in time current value obtained for the multiple excitations. The maximum kinetic performance may be reached at the first excitation having decaying current values, or it may be reached at a subsequent excitation, such as the second, third or later excitation having decaying current values.

The maximum kinetic performance can be described in terms of the parameter "peak time", which is the time at which an electrochemical test sensor obtains its maximum output current value after a sample containing an analyte contacts the test sensor. The maximum output current value is preferably used for correlation with the analyte concentration of the sample. Preferably the peak time for a test sensor is less than about 7 seconds, and more preferably less than about 5 seconds, of introducing the sample to the test sensor. Preferably, the peak time is within about 0.4 to about 7 seconds, more preferably within about 0.6 to about 6.4 seconds, more preferably within about 1 to about 5 seconds, and more preferably within about 1.1 to about 3.5 seconds of introducing the sample to the test sensor.

Referring to FIG. 1A, test sensors that had been sealed in a container having the conventional desiccant had longer peak times after being stored at 50° C. for two weeks (peak time=~3.5 seconds) than after being stored at −20° C. for two weeks (peak time=~2 seconds). In contrast, the sensors sealed either with silica gel desiccant (FIG. 1B) or with no desiccant (FIG. 1C) had no increase in their peak times when stored at 50° C. for two weeks relative their storage at −20° C. for two weeks (peak times=~2 seconds). Thus, storing test sensors with a conventional desiccant led to a 75% increase (75%=100%×[(3.5 sec−2 sec)/2 sec]) in the time required to obtains the maximum output current value when the storage temperature was increased from −20° C. to 50° C., whereas test sensor stored with silica gel desiccant or no desiccant showed a 0% increase in the time required to obtains the maximum output current value when the storage temperature was increased from −20° C. to 50° C.

Any change in the current profile of a test sensor can lead to inconsistent glucose assay results, as test sensor glucose results typically are derived from the measured output current at a fixed time point. This increased inaccuracy is especially evident for assays performed at shorter times, such as 10 seconds or less. For the test sensors examined for FIGS. 1A-1C, the change in the current profile for the test sensors sealed with the conventional desiccant resulted in an undesirable increase in bias of the biosensor.

The measurement performance of a biosensor system is defined in terms of its accuracy and/or precision. Accuracy reflects the combined effects of random and systematic error components. Systematic error, or trueness, is the difference between the average value determined from the biosensor system and one or more accepted reference values for the analyte concentration of the sample. Trueness may be expressed in terms of mean bias, with larger mean bias values representing lower trueness and thereby contributing to less accuracy. Precision reflects the closeness of agreement among multiple analyte readings in relation to a mean. One or more errors in the analysis contribute to the bias and/or imprecision of the analyte concentration determined by the biosensor system. A reduction in the analysis error of a biosensor system therefore leads to an increase in accuracy and thus an improvement in measurement performance.

Bias may be expressed in terms of "absolute bias" or "percent bias", depending on the analyte concentration in the sample. Absolute bias may be expressed in the units of the measurement, such as mg/dL, and may be used for analyte concentrations less than 100 mg/dL. Percent bias may be expressed as a percentage of the absolute bias value over a reference value, and may be used for analyte concentrations of at least 100 mg/dL. Accepted reference values may be obtained with a reference instrument, such as the YSI 2300 STAT PLUS™ glucose analyzer available from YSI Inc., Yellow Springs, Ohio.

The percent of analyses that fall within a "bias limit" of a selected bias boundary indicate the percent of the determined analyte concentrations that are close to a reference concentration. Thus, the limit defines how close the determined analyte concentrations are to the reference concentration. The bias limit may be expressed as an absolute bias limit for analyte concentrations less than 100 mg/dL, or as a percent bias limit for analyte concentrations of at least 100 mg/dL. For instance, 95 out of 100 performed analyses (95%) falling within a ±10% bias limit is a more accurate result than 80 out of 100 performed analyses (80%) falling within a ±10% bias limit. Similarly, 95 out of 100 performed analyses falling within a ±5% bias limit is a more accurate result than 95 out of 100 performed analyses falling within a ±10% bias limit. Thus, an increase in the percentage of analyses falling within a selected bias limit, or within a narrower bias limit, represents an increase in the measurement performance of the biosensor system.

Figure 2A:
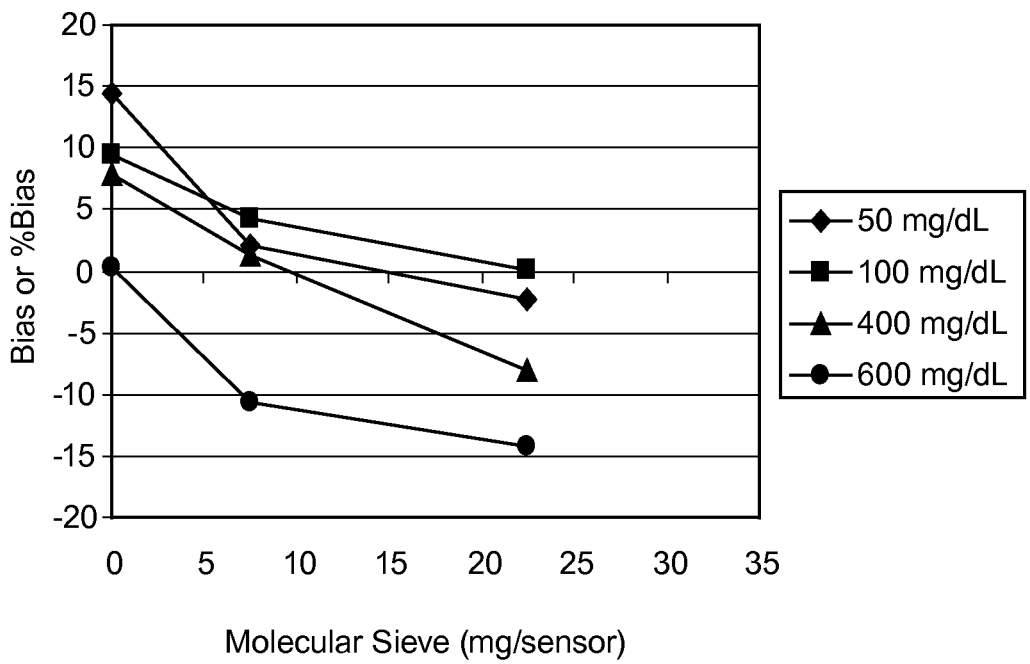
FIGS. 2A and 2B represent graphs of assay bias for glucose assays of whole blood samples having glucose concentrations of 50, 100, 400 or 600 mg/dL. The test sensors were sealed with various levels of molecular sieve desiccant (2A) or silica gel desiccant (2B).
Figure 2B:
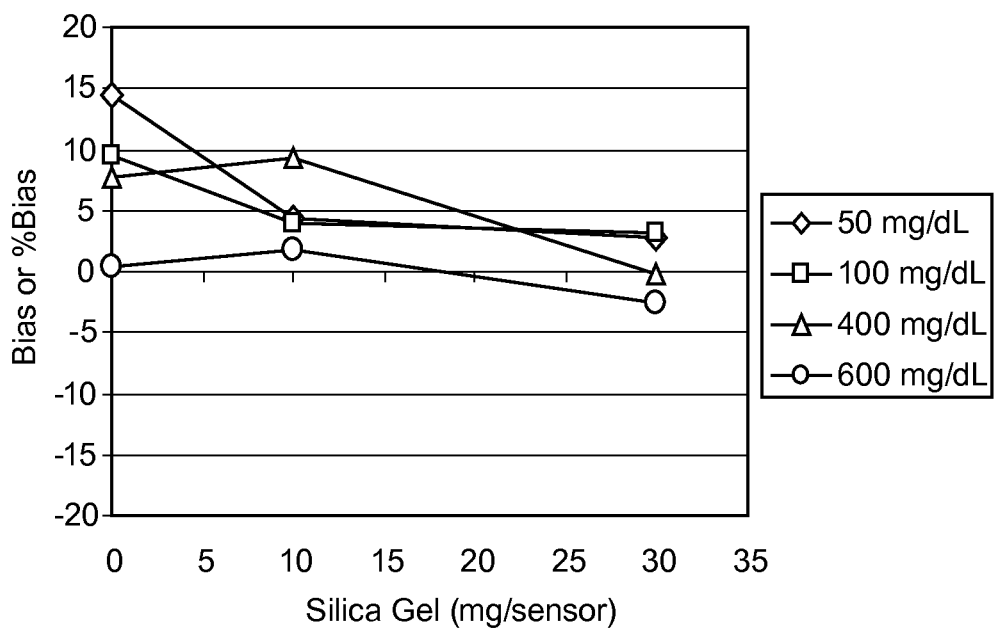

FIGS. 2A and 2B depict graphs of bias (absolute bias or percent bias) for glucose assays of whole blood samples having hematocrit contents of 40% and having glucose concentrations of 50, 100, 400 or 600 mg/dL. The test sensors used in the analysis were sealed, in groups of 50 test sensors, in containers having from 0 to 22.5 mg per test sensor of the conventional desiccant molecular sieve 13x (FIG. 2A), or containing from 0 to 30 mg per test sensor of silica gel (FIG. 2B), and were stored at 50° C. for two weeks. After the storage period, test sensors were removed from their container, connected through their conductors to a measurement device, and then contacted with one of the whole blood samples.

Without desiccant (0 mg desiccant/test sensor), the blood glucose assays after the test sensor heat stress had a positive bias of 15 mg/dL for samples containing low glucose (50 mg/dL), 7-10% bias for samples having glucose concentrations of 100 mg/dL and 400 mg/dL, and had almost no bias for samples containing high glucose (600 mg/dL). Sealing the test sensors with the conventional molecular sieve desiccant (FIG. 2A) corrected the positive bias for samples with low and normal glucose; however, the bias for samples with 600 mg/dL glucose increased to −10% and −15% bias as the desiccant level increased. In contrast, the bias for sensors stored with 30 mg/sensor silica gel was within 5 mg/dL bias for samples having less than 100 mg/dL glucose, and was within ±5% bias for samples having 100 mg/dL to 600 mg/dL glucose (FIG. 2B).

The increase in assay peak time (FIG. 1A) and in assay bias (FIG. 2A) for test sensors sealed at 50° C. for two weeks in the presence of a conventional desiccant is surprising when compared to the results for similarly treated test sensors sealed with no desiccant (FIG. 1C) or with the weaker desiccant of silica gel (FIGS. 1B, 2B). Typically, desiccants have been used to prevent transformations of components of the reagent composition, including the mediator, prior to use of the test sensor. Thus, it would be unexpected that storage of a test sensor with a conventional desiccant would impair the test sensor's accuracy and/or its shelf-life, relative to that of a comparable test sensor stored with no desiccant or with a less aggressive desiccant, especially when analyzing samples having high analyte concentrations.

For a biosensor system that includes a plurality of test sensors sealed in a container having a desiccant, the accuracy of the system may be evaluated by using the test sensors to determine the analyte content of samples having known concentrations of the analyte that span a certain range of concentrations, and then calculating the bias of the determinations with regard to the actual concentrations. In such an evaluation, a plurality of test sensors is sealed in a container including a desiccant for two weeks at a temperature of 50° C., where each test sensor includes at least two conductors, one of which is a working electrode, and a reagent composition disposed on or near the working electrode. Each test sensor is then removed from the container, connected through the at least two conductors to a measurement device, contacted with one of the samples having a known analyte content, and used to determine the analyte concentration in the sample.

In this example, for samples having an analyte concentration that spans the range of 50 mg/dL-600 mg/dL, preferably 95% of the determined analyte concentrations less than 100 mg/dL are within a ±10 mg/dL bias limit, and 95% of the determined analyte concentrations of at least 100 mg/dL are within a ±10% percent bias limit. The phrase "an analyte concentration that spans the range of 50 mg/dL-600 mg/dL" means that at least one of the samples has an analyte concentration of 50 mg/dL, and at least one of the other samples has an analyte concentration of 600 mg/dL. The remaining samples, if any, may have analyte concentrations between 50 mg/dL and 600 mg/dL. More preferably 97%, 99% or 100% of the determined analyte concentrations less than 100 mg/dL are within a ±10 mg/dL bias limit, and 97%, 99% or 100% of the determined analyte concentrations of at least 100 mg/dL are within a ±10% percent bias limit.

In the above example, preferably 95%, 97%, 99% or 100% of the determined analyte concentrations less than 100 mg/dL are within a ±7 mg/dL bias limit, and 95%, 97%, 99% or 100% of the determined analyte concentrations of at least 100 mg/dL are within a ±7% percent bias limit. More preferably 95%, 97%, 99% or 100% of the determined analyte concentrations less than 100 mg/dL are within a ±5 mg/dL bias limit, and 95%, 97%, 99% or 100% of the determined analyte concentrations of at least 100 mg/dL are within a ±5% percent bias limit. Preferably, in this example the number of test sensors sealed in a container is at least 5, and preferably is at least 10, at least 25, at least 50, or at least 100. Preferably, in this example the samples have analyte concentrations that span the range of 10 mg/dL-600 mg/dL.

The precision of a biosensor system may be expressed in terms of the spread or variance of the bias among multiple determined analyte concentrations relative to a mean. A mean and a standard deviation may be calculated for multiple analyses using test sensors, where the standard deviation describes the spread of the multiple analyses from each other. A coefficient of variation (% CV) may be calculated from the mean and the standard deviation, where the % CV is defined as (standard deviation/mean)*100%. A lower spread of the determined analyte concentrations is reflected in a smaller standard deviation, which in turn results in a smaller % CV.

Thus, % CV may be considered an indicator of the precision of multiple analyses, and a decrease in % CV represents an increase in the measurement performance of the biosensor system.

For a biosensor system that includes a plurality of test sensors sealed in a container having a desiccant, the precision of the system may be evaluated by using the test sensors to determine the analyte content of samples having a known concentration of the analyte, and then calculating the % CV of the determinations. In such an evaluation, a plurality of test sensors is sealed in a container including a desiccant for two weeks at a temperature of 50° C., where each test sensor includes at least two conductors, one of which is a working electrode, and a reagent composition disposed on or near the working electrode. Each test sensor is then removed from the container, connected through the at least two conductors to a measurement device, contacted with one of the samples having a known analyte content, and used to determine the analyte concentration in the sample. The % CV of the determined analyte concentrations is then calculated. In this example, the % CV for the determined analyte concentrations preferably is at most 2.5%. More preferably the % CV for the determined analyte concentrations is at most 2%.

Table 1 lists the % CV for glucose assays of whole blood samples having hematocrit contents of 42% and having glucose concentrations of 50, 100, 400 or 600 mg/dL. The test sensors used in the analysis were sealed, in groups of 50 test sensors, in containers either having no desiccant, having 7.5 or 22.5 mg per test sensor of the conventional desiccant molecular sieve 13x, or having 10 or 30 mg per test sensor of silica gel desiccant. The containers were stored at 50° C. for two weeks. After the storage period, test sensors were removed from their container, connected through their conductors to a measurement device, contacted with one of the whole blood samples, and used to determine the glucose concentrations in the samples. Each result listed is based on determinations using 10 test sensors.

TABLE 1

Assay Precision for Test Sensors Heat Stressed at 50° C. for 2 Weeks

| Desiccant | | % CV (%) for glucose concentrations: | | | |
|---|---|---|---|---|---|
| Type | Amount (mg/sensor) | 50 mg/dL | 100 mg/dL | 400 mg/dL | 600 mg/dL |
| None | 0 | 1.9 | 1.8 | 2.4 | 1.3 |
| Molecular Sieves | 7.5 | 2.4 | 4.9 | 1.5 | 2.8 |
|  | 22.5 | 2.9 | 2.4 | 2.1 | 2.0 |
| Silica gel | 10.0 | 3.3 | 1.6 | 2.5 | 1.4 |
|  | 30.0 | 1.5 | 1.1 | 1.3 | 1.1 |

Table 2 lists the % CV for glucose assays as described for Table 1, but where the test sensors were stored at −20° C. for two weeks. Each result listed is based on determinations using 10 test sensors.

TABLE 2

Assay Precision for Test Sensors Stored at −20° C. for 2 Weeks

| Desiccant | | % CV (%) for glucose concentrations: | | | |
|---|---|---|---|---|---|
| Type | Amount (mg/sensor) | 50 mg/dL | 100 mg/dL | 400 mg/dL | 600 mg/dL |
| None | 0 | 2.9 | 2.9 | 1.6 | 1.0 |
| Molecular | 7.5 | 1.3 | 1.5 | 3.4 | 1.3 |
| Sieves | 22.5 | 5.8 | 4.2 | 1.9 | 1.5 |
| Silica gel | 10.0 | 1.8 | 3.3 | 1.6 | 1.3 |
|  | 30.0 | 1.8 | 2.1 | 2.0 | 1.3 |

Without desiccant (0 mg desiccant/test sensor), the blood glucose assays after the test sensor heat stress (2 weeks at 50° C.) had % CV values of 1.3-2.4% for samples having analyte concentrations that spanned the range of 50 mg/dL-600 mg/dL (first row of results in Table 1). Sealing the test sensors with the conventional molecular sieve desiccant (7.5 or 22.5 mg/test sensor) or with 10 mg/test sensor silica gel did not reduce the upper limit of % CV for the blood glucose assays (4.9%, 2.9% and 3.3%, respectively; $2^{nd}$-$4^{th}$ rows of results in Table 1). Sealing the test sensors with 30 mg/test sensor silica gel, however, did reduce the upper limit of % CV for the blood glucose assays to 1.5% (% CV range of 1.1-1.5%; last row of results in Table 1).

A similar trend regarding % CV values was also measured for blood glucose assays after the test sensors had been sealed at −20° C. for 2 weeks. Without desiccant (0 mg desiccant/test sensor), the blood glucose assays after being sealed for 2 weeks at −20° C. had % CV values of 1.0-2.9% for samples having analyte concentrations that spanned the range of 50 mg/dL-600 mg/dL (first row of results in Table 2). Sealing the test sensors with the conventional molecular sieve desiccant (7.5 or 22.5 mg/test sensor) or with 10 mg/test sensor silica gel did not reduce the upper limit of % CV for the blood glucose assays (3.4%, 5.8% and 3.3%, respectively; $2^{nd}$-$4^{th}$ rows of results in Table 2). Sealing the test sensors with 30 mg/test sensor silica gel, however, did reduce the upper limit of % CV for the blood glucose assays to 2.1% (% CV range of 1.3-2.1%; last row of results in Table 2). For both sets of storage conditions—2 weeks at 50° C. or 2 weeks at −20° C.—blood glucose assays performed using test sensors sealed with 30 mg/test sensor silica gel had % CV values of at most 2.1% for samples having analyte concentrations that spanned the range of 50 mg/dL-600 mg/dL.

These differences between the % CV values of test sensors stored with conventional molecular sieve desiccant and the % CV values of test sensors stored with silica gel were statistically significant. For example, the % CV values of the determined glucose concentrations from test sensors stored with 30 mg/sensor silica gel for 2 weeks at 50° C. (last row of results in Table 1) were significantly lower than the % CV values of the determined glucose concentrations from test sensors stored with 22.5 mg/sensor molecular sieve desiccant for 2 weeks at 50° C. ($3^{rd}$ row of results in Table 1), with a confidence level of at least 90%, for concentrations that spanned the range of 50 mg/dL-600 mg/dL. The % CV values of the determined glucose concentrations from test sensors stored with 30 mg/sensor silica gel for 2 weeks at 50° C. (last row of results in Table 1) were significantly lower than the % CV of the determined glucose concentrations from test sensors stored with 22.5 mg/sensor molecular sieve desiccant for 2 weeks at 50° C. ($3^{rd}$ row of results in Table 1), with a confidence level of at least 95%, for concentrations that spanned the range of 50 mg/dL-100 mg/dL.

Figure 3A:
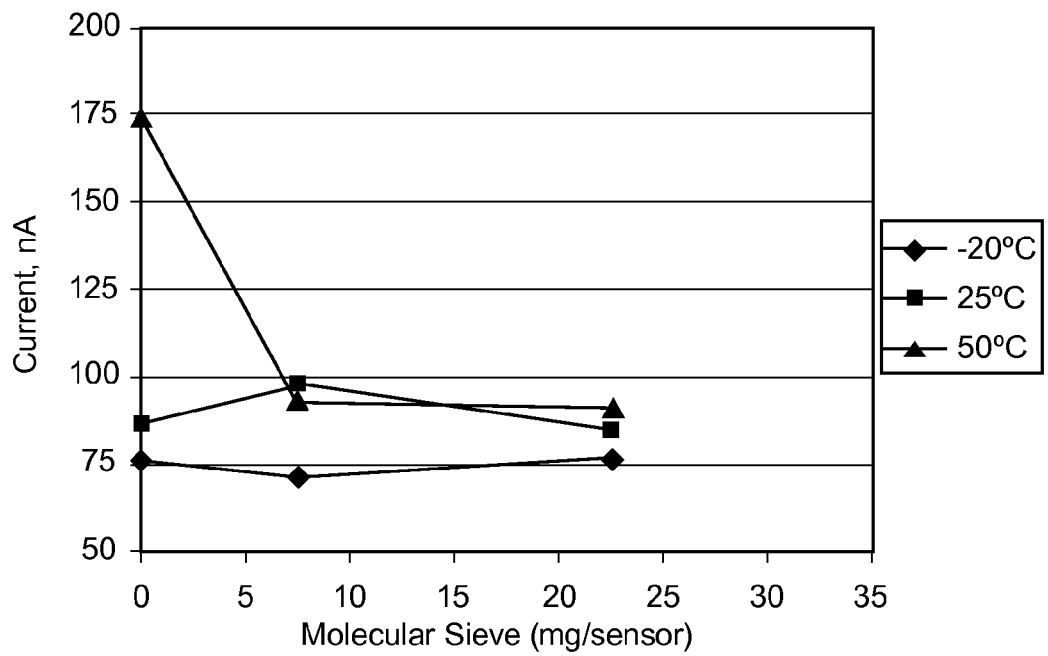
FIGS. 3A and 3B represent graphs of background current for glucose assays of whole blood samples containing no glucose, for test sensors sealed in containers having varying levels of molecular sieve desiccant (3A) or silica gel desiccant (3B), and stored for 2 weeks at various temperatures.
Figure 3B:
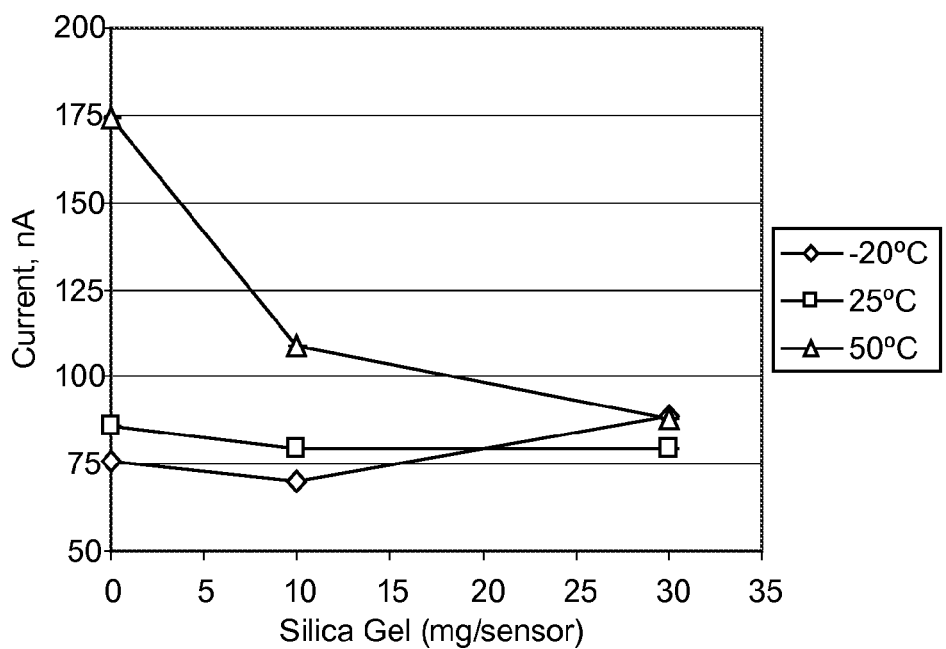

FIGS. 3A and 3B depict graphs of background current for glucose assays of whole blood samples containing no glucose. The test sensors used in the analysis were sealed in containers either having no desiccant, having 7.5 or 22.5 mg per test sensor of the conventional desiccant molecular sieve 13x (FIG. 3A), or having 10 or 30 mg per test sensor of silica gel desiccant (FIG. 3B), and were stored for two weeks at −20° C., at room temperature (25° C.) or at 50° C. After the storage period, test sensors were removed from their container, connected through their conductors to a measurement device, and contacted with one of the whole blood samples. As the samples contained no glucose, the measured background current was due to the presence of substances in reduced oxidation states, such as reduced mediator.

Test sensors stored without desiccant in the container (0 mg desiccant/sensor in FIGS. 3A and 3B) showed a large increase in biosensor background current after the heat stress, as the background current increased from ~90 nanoamps (nA) at 25° C. to ~175 nA at 50° C. This increase was consistent with the conventional theory that a desiccant is important to maintain low background current in the test sensor, likely by preventing auto-reduction of the mediator. An increase in sensor background current may have contributed to the positive assay bias represented in FIGS. 2A and 2B for samples with lower glucose concentrations of 50 or 100 mg/dL. Test sensors stored in the presence of the conventional molecular sieve desiccant (FIG. 3A) required less of the desiccant to maintain a low background current (7.5 mg/sensor) than did test sensors stored in the presence of silica gel (10 mg/sensor; FIG. 3B). Thus, the conventional desiccant appeared to accomplish its intended function of inhibiting premature reduction of the mediator.

In the example of FIG. 3A, test sensors stored with the conventional desiccant at 50° C. for two weeks had a background current approximately within ±30% (7.5 mg/sensor) or approximately within ±20% (22.5 mg/sensor) of the measured background current of identical test sensor stored with the conventional desiccant at −20° C. for two weeks (~30%=[(90 nA−70 nA)/70 nA]×100%; ~20%=[(90 nA−75 nA)/75 nA]×100%). In the example of FIG. 3B, test sensors stored with 30 mg/sensor silica gel desiccant at 50° C. for two weeks had a background current approximately within ±10% of the measured background current of identical test sensor stored with the conventional desiccant at −20° C. for two weeks (~10%=[(85 nA−80 nA)/80 nA]×100%.

Thus, for a biosensor system that includes a plurality of test sensors sealed in a container, the premature reduction of the mediator during storage may be evaluated by measuring background current in an electrochemical analysis using the test sensors with samples containing no analyte. In such an evaluation, a plurality of test sensors is sealed in a container for two weeks at a temperature of 50° C., where each test sensor includes at least two conductors, one of which is a working electrode, and a reagent composition containing a mediator disposed on or near the working electrode. Each test sensor is then removed from the container, connected through the at least two conductors to a measurement device and contacted with a sample containing no analyte, and then used to measure the background current. Preferably the measured background current is within ±20% of the measured background current of an identical test sensor that had instead been stored for two weeks at −20° C. Preferably the measured background current is within ±10% or within ±5% of the measured background current of an identical test sensor that had instead been stored for two weeks at −20° C.

The mediator in the reagent compositions of the test sensors used in FIGS. 1 through 5 was the two electron transfer mediator 3-(2',5'-disulfophenylimino)-3H-phenothiazine bis-sodium salt. The observed effects of moisture during storage of test sensors are believed to apply to other two electron transfer mediators, such as other organic quinones and hydroquinones. Examples of such mediators include phenathroline quinone; phenothiazine and phenoxazine derivatives, such as 3-phenylimino-3H-phenothiazines (PIPT) and 3-phenylimino-3H-phenoxazines (PIPO); 3-(phenylamino)-3H-phenoxazines; phenothiazines; and 7-hydroxy-9,9-dimethyl-9H-acridin-2-one and its derivatives. The observed effects of moisture during storage of test sensors also are believed to apply to one electron transfer mediators such as 1,1'-dimethyl ferrocene, ferrocyanide and ferricyanide, ruthenium(III) and ruthenium(II) hexaamine.

One possible explanation for the surprising results regarding peak time, bias and/or precision is that a less aggressive desiccant can provide unexpectedly good protection of an enzyme in a test sensor reagent composition. A less aggressive desiccant, such as silica gel, appeared to be more compatible with the FAD-GDH enzyme than was the conventional desiccant, yet the less aggressive desiccant still provided sufficient protection for the mediator. The impact of the loss of enzyme activity on biosensor measurement performance may have been underestimated previously, particularly for high glucose samples.

Figure 4:
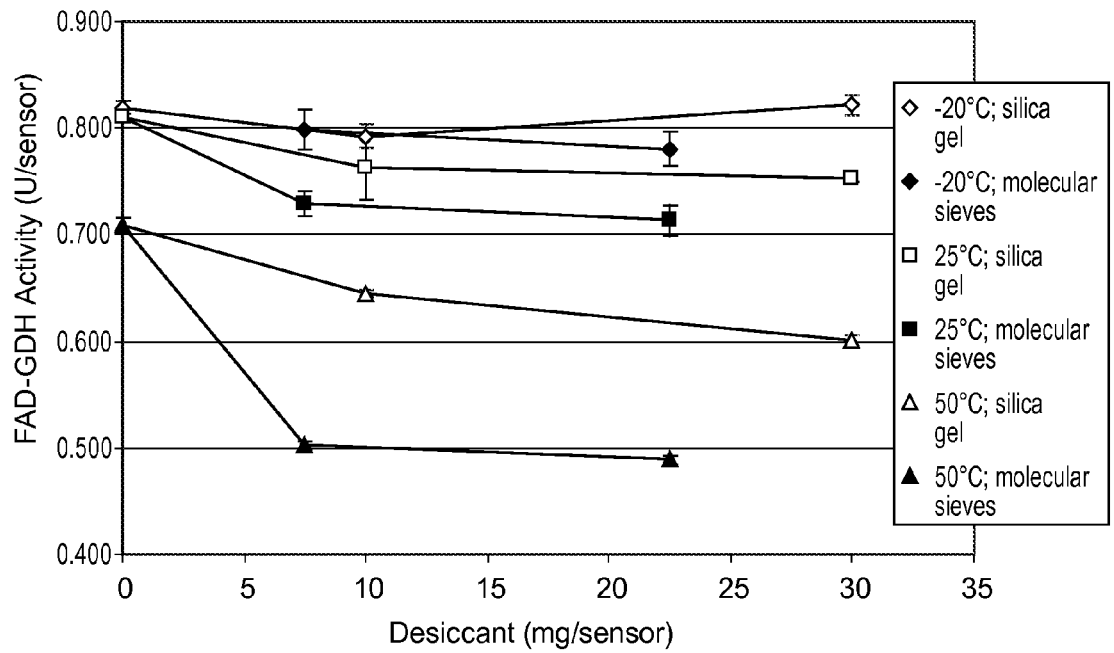
FIG. 4 represents a graph of in-sensor enzyme activity for test sensors sealed in containers having varying types and levels of desiccant and stored for two weeks either at −20° C., at 50° C., or at room temperature (25° C.).

FIG. 4 depicts graphs of in-sensor FAD-GDH enzyme activity for test sensors sealed for two weeks either at −20° C. (diamond symbols), at 50° C. (triangle symbols) or at room temperature (square symbols), in containers having varying types and levels of desiccant. The solid symbols correspond to conventional molecular sieve desiccant, and the open symbols correspond to silica gel desiccant. Neither desiccant appeared to allow significant loss of enzyme activity at −20° C. After storage at 50° C. for two weeks, there was an approximately 13% loss in sensor enzyme activity for sensors sealed in a container without a desiccant (0 mg desiccant/sensor; 13.4%=100%×[(0.819 U/sensor−0.709 U/sensor)/0.819 U/sensor]). The enzyme activity decreased by approximately 40% for sensors sealed in a container with the conventional molecular sieve desiccant (solid triangle symbols) for two weeks at 50° C., even at relatively low levels of 7.5 mg desiccant per sensor (38.7%=100%×[(0.819 U/sensor−0.502 U/sensor)/0.819 U/sensor]; for 22.5 mg/sensor, 40.3%=100%×[(0.819 U/sensor−0.489 U/sensor)/0.819 U/sensor]). In contrast, the retained enzyme activity for sensors sealed for two weeks at 50° C. in a container with 10 mg silica gel desiccant (open triangle symbol) was higher than that of the sensors sealed with 7.5 mg conventional desiccant by approximately 28% (28.3%=100%×[(0.644 U/sensor−0.502 U/sensor)/0.502 U/sensor]). After storage at 50° C. for two weeks, the sensors sealed with silica gel desiccant retaining enzyme activities of approximately 73-79% (open triangle symbols; 73.4% retention corresponds to 26.6% decrease=100%×[(0.819 U/sensor−0.601 U/sensor)/0.819 U/sensor]; 78.6% retention corresponds to 21.4% decrease=100%×[(0.819 U/sensor−0.644 U/sensor)/0.819 U/sensor]). Even for room temperature storage, test sensors sealed in a container with the conventional molecular sieve desiccant (solid square symbols) showed retained enzyme activities that were approximately 5% lower than those retained by test sensors sealed in a container with silica gel desiccant (open square symbols; i.e. 4.5%=100%×[(0.763 U/sensor−0.729 U/sensor)/0.763 U/sensor]; 5.2%=100%×[(0.753 U/sensor−0.714 U/sensor)/0.753 U/sensor]).

The results of FIG. 4, combined with the results of FIGS. 1 through 3, are consistent with an analysis that the FAD-GDH enzyme requires a minimum level of moisture to maintain its native structure and activity. In the example of sensors sealed in a container with conventional molecular sieve desiccant and subsequently used to determine glucose concentrations of 600 mg/dL, the increase in negative bias with increasing molecular sieve desiccant (FIG. 2A) correlated with an approximately 40% loss in FAD-GDH enzyme activity (FIG. 4). In contrast, for sensors sealed in a container with silica gel desiccant and subsequently used to determine glucose concentrations of 600 mg/dL the relatively constant and near-zero bias with increasing silica gel desiccant (FIG. 2B) correlated with only a 21-27% loss in FAD-GDH enzyme activity (FIG. 4).

Table 3 lists the in-sensor FAD-GDH enzyme activity ("% enzyme recovery") for test sensors sealed for two weeks at 50° C. in containers having varying types of desiccant. These test sensors included either a reagent composition containing sorbitol as an enzyme stabilizer, or a reagent composition without an enzyme stabilizer. The desiccants used were silica gel, molecular sieve 13x (MS-13x), and a bottle sleeve containing molecular sieve 4 A. The "molecular sieve 4 A" desiccant included a sodium alumino-silicate having a "type A" crystal structure containing an effective pore opening of approximately 4 angstroms. The reagent composition for the control test sensors was formed by deposition and drying of a reagent fluid that included water, 80 millimolar (mM) 3-(2', 5'-disulfophenylimino)-3H-phenothiazine bis-sodium salt mediator, 3.75 enzyme units FAD-GDH per microliter, 0.2% (w/w) hydroxyethyl cellulose (HEC) binder having a weight average molecular weight ($M_w$) of 300,000, 0.362% (w/w) HEC binder having a $M_w$ of 90,000, 112.5 mM $Na_2HPO_4$ buffer salt, 0.225% (w/w)N-octanoyl-N-methyl-D-glucamine (MEGA-8), and 0.01% (w/w) sodium methyl cocoyl taurate (Geropon TC-42). The reagent composition for test sensors labeled "Sorbitol" was formed as for the control sensors, except that the reagent fluid also included 0.4% (w/w) sorbitol.

TABLE 3

Effect of Desiccant and Reagent Composition on Enzyme Activity

| Desiccant | % Enzyme Recovery | |
|---|---|---|
| | Control | Sorbitol |
| Silica gel | 83.8 | 89.4 |
| Molecular sieve 13x | 73.4 | 82.1 |
| Bottle sleeve containing molecular sieve 4A | 74.0 | 79.0 |

In this example, test sensors sealed in a container with pure molecular sieve desiccant or a bottle sleeve desiccant had a decrease in enzyme activity of 26.6% and 26%, respectively. In contrast, test sensors sealed in a container with silica gel desiccant had only a 16.2% decrease in enzyme activity. Thus, replacing the molecular sieve or bottle sleeve desiccant with a silica gel desiccant provided an improvement in enzyme stability of 38-39% (39%=100% [(26.6%−16.2%)/26.6%]; 38%=100% [(26%−16.2%)/26%]). Stabilization of the enzyme in the reagent composition with 0.4% sorbitol diminished the loss of enzyme activity for each of the desiccants. The sorbitol-stabilized test sensors sealed with molecular sieve desiccant or a bottle sleeve desiccant, however, allowed for approximately twice the amount of enzyme inactivation allowed by the silica gel desiccant (17.9% inactivation for conventional molecular sieves and 21% inactivation for bottle sleeve, versus 10.6% inactivation for silica gel).

Table 4 lists the in-sensor FAD-GDH enzyme activity ("% enzyme recovery") for test sensors sealed for two weeks at 50° C. in containers having varying types of desiccant. The desiccants used were silica gel, molecular sieve 13x, and two different polymer-blended desiccants—a polypropylene film coated with molecular sieves, and a polypropylene film coated with silica gel. The polymer-blended desiccants were obtained from Multisorb Technologies (Buffalo, N.Y.). The reagent composition for the test sensors was formed by deposition and drying of a reagent fluid prepared according to that of the control test sensors of Table 3, above.

TABLE 4

Effect of Desiccant on Enzyme Activity

| Desiccant | % Enzyme Recovery |
|---|---|
| Silica gel | 86.4 |
| Molecular sieve 13x | 76.1 |
| Polypropylene film with molecular sieve | 83.0 |
| Polypropylene film with silica gel | 87.1 |

In this example, blending of molecular sieve desiccant with polypropylene provided for retention of enzyme activity of 83%, which was comparable to that provided by the silica gel desiccant (86.4%). Thus, inhibiting the desiccating ability of the molecular sieves allowed the enzyme to retain its activity during the heat stress.

Thus, for a biosensor system that includes a plurality of test sensors sealed in a container having a desiccant, the system may be evaluated by measuring the retention of redox enzyme activity in the reagent composition of the test sensors after the test sensors are stored in various conditions. In such an evaluation, a plurality of test sensors is sealed in a container including a desiccant for two weeks at a temperature of 50° C., where each test sensor includes at least two conductors, one of which is a working electrode, and a reagent composition including a redox enzyme having an activity disposed on or near the working electrode. The test sensors are then removed from the container, and the activity of the redox enzyme in the reagent composition of each test sensor is measured. In this example, the reagent composition of each test sensor preferably retains at least 75% of the activity of the redox enzyme. More preferably, in this example the reagent composition of each test sensor preferably retains at least 80% of the activity of the redox enzyme, and more preferably retains at least 85% of the activity of the redox enzyme. Preferably, in this example the number of test sensors in the plurality is at least 5, and preferably is at least 10, at least 25, at least 50, or at least 100.

The correlation of one or more output current values, such as the output current values depicted in FIGS. 1A-1D, with the analyte concentration of the sample may be adjusted to account for errors in the measurement. One approach to correct errors associated with a biosensor analysis is to adjust the correlation for determining analyte concentrations in a sample from output current values, using index functions extracted from intermediate current values of the output current values. Index functions can compensate the correlation for determining analyte concentrations from the output current values for one or more errors in the analyses that could result in bias of the determined analyte concentrations. Index functions correspond to the bias in the correlation between the analyte concentrations and the output current values due to one or more errors in the analysis.

Bias in an analyte concentration determination may be represented by one or more ΔS values obtained from one or more error parameters. The ΔS values represent slope deviations of the correlation between analyte concentrations and output current values determined from one or more error parameters. The slope of the correlation corresponds to the change in output current for a given change in sample analyte concentration. Index functions corresponding to the slope or change in slope may be normalized to reduce the statistical effect of changes in the output current values, improve the differentiation in variations of the output current values, standardize the measurements of the output current values, a combination thereof, or the like. The adjusted correlation may be used to determine analyte concentrations in biological samples from the output current values and may have improved accuracy and/or precision in comparison to conventional biosensors. Error correction using index functions and $\Delta S$ values is described, for example, in U.S. Patent Pub. 2009/0177406 to Wu, entitled "Slope-Based Compensation"; and in International Patent Application No. PCT/US2009/067150, filed Dec. 8, 2009, entitled "Complex Index Functions", published as WO 2010/077660. The disclosures of these patent applications regarding error correction using index functions and $\Delta S$ values are herein incorporated by reference.

Index functions may include ratios extracted from an output signal, such as the output signals depicted in FIGS. 1A-1D. For example, the intermediate output signal values may be compared within an individual pulse-signal decay cycle, such as ratio $R3=i_{3,3}/i_{3,1}$, and the like, where $i_{3,3}$ denotes the third current value recorded for the third signal decay, and $i_{3,1}$ denotes the first current value recorded for the third signal decay. In another example, the intermediate output signal values may be compared between separate pulse-signal decay cycles, such as ratio $R4/3=i_{4,3}/i_{3,3}$, and the like, where $i_{4,3}$ denotes the third current value recorded for the fourth signal decay.

Index functions may include combinations of ratios extracted from the output signal, such as the output signals depicted in FIGS. 1A-1D. In one example, an index function may include a ratio of ratios, such as Ratio3/2=R3/R2, Ratio4/3=R4/R3, and the like. In another example, an index function may include a combination of indices. For example, a combination index, Index-1, may be represented as Index-1=R4/3-Ratio3/2. In another example, a combination index function Index-2 may be represented at Index-2=$(R4/3)^p$-$(Ratio3/2)^q$, where p and q independently are positive numbers.

An index function is complex when the function includes a combination of terms modified by weighing coefficients. The combination is preferably a linear combination, but other combination methods may be used that provide weighing coefficients for the terms. Each term may include one or more error parameters. An example of a complex index function is represented as follows:

$$f(CIndex) = a_1 + (a_2)(R3/2) + \\ (a_3)(R4/3) + (a_4)(R5/4) + (a_5)(R3/2)(G_{raw}) + \\ (a_6)(R4/3)(G_{raw}) + (a_7)(R3/2)(Temp) + \\ (a_8)(R4/3)(Temp) + (a_9)(Temp) + (a_{10})(G_{raw}) + \ldots ,$$

(Equation 1)

where $a_1$ is a constant, $a_2$-$a_{10}$ independently are weighing coefficients, $G_{raw}$ is the determined analyte concentration of the sample without compensation, and Temp is temperature. Each of the weighing coefficients ($a_2$-$a_{10}$) is followed by its associated term.

There are at least three basic types of terms in the complex index function represented by Equation 1: (1) the individual ratio indices extracted from the output signal, such as R3/2 and R4/3, (2) the interaction terms between the ratio indices extracted from the output signal and the temperature or $G_{raw}$, such as $(R3/2)(G_{raw})$ and (R3/2)(Temp), and (3) temperature and $G_{raw}$. The terms may include values other than error parameters, including $G_{raw}$. Other terms also may be used, including, but not limited to a combination index function, as previously described. The complex index function may be solved to provide a complex index value when the terms are replaced with the appropriate values. Statistical processing may be performed on the multiple terms to determine one or more constants and weighing coefficients. Statistical package software, including MINITAB (MINITAB, INC., State College, Pa.), may be used to perform the statistical processing.

The constant $a_1$ may be determined by regression or other mathematical technique. While a single constant is shown in Equation 1, a constant is not required; more than one may be used, and may be equal to 0. Thus, one or more constants may or may not be included in the complex index function.

A complex index function includes at least two terms that are modified by weighing coefficients, which provides the ability to individually weigh the contribution of the terms to the index function. Weighing coefficients are numerical values other than one or zero. Preferably, each term including an error parameter is modified by a weighing coefficient. More preferably, each non-constant term of the complex index function is modified by a weighing coefficient. Weighing coefficients may have positive or negative values. Weighing coefficients may be determined through the statistical processing of the experimental data collected from a combination of multiple analyte concentrations, different hematocrit levels, different temperatures, and the like.

Preferably an index function in a glucose assay corrects errors associated with variations in hematocrit content. For example, conventional biosensor systems may be configured to report glucose concentrations presuming a 40% (v/v) hematocrit content for a whole blood sample, regardless of the actual hematocrit content of the sample. In these systems, any glucose measurement performed on a blood sample containing less or more than 40% hematocrit will include error and thus have bias attributable to the hematocrit effect.

Calculation of an index function that corrects errors associated with variations in hematocrit content can be facilitated by using a test sensor that produces an output signal that varies with hematocrit content. For some biosensors, the R5/4 ratio parameter has served as an indicator of hematocrit in a sample, and has been used to adjust the measured analyte concentration to account for the hematocrit content of the sample. The R5/4 ratio parameter represents the relationship between the currents generated by the analyte in response to the $4^{th}$ and $5^{th}$ pulses of a gated amperometric pulse sequence, such as the sequences of FIGS. 1A-1D.

Figure 5:
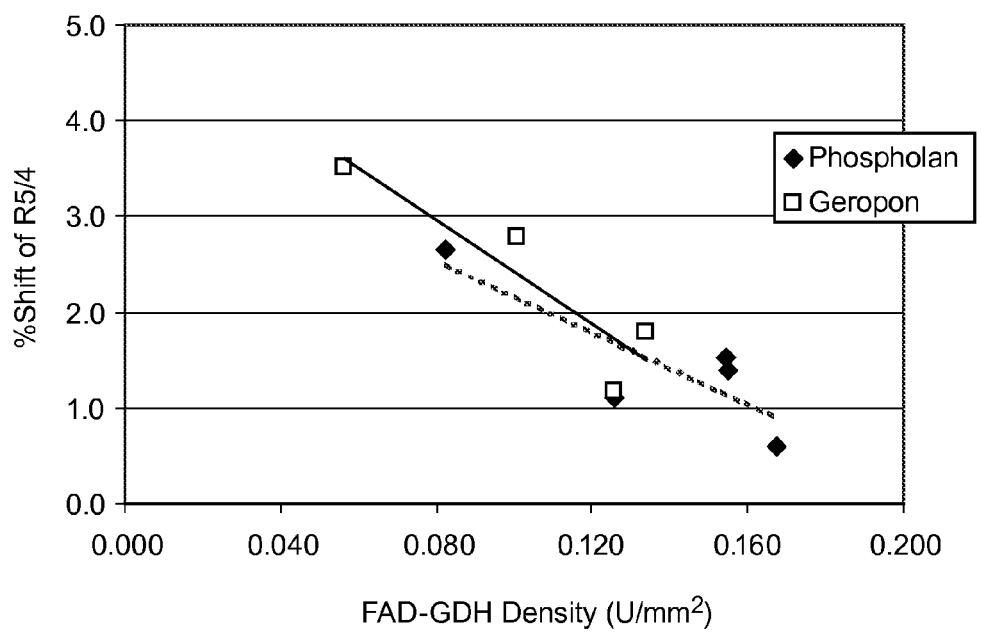
FIG. 5 represents graphs of the variation of the R5/4 ratio parameter for test sensors sealed in a container and stored for two weeks at 50° C., relative to the R5/4 ratio parameter for test sensors stored sealed in a container and stored for two weeks at −20° C., where the test sensors had varying levels of enzyme density above the working electrode of the test sensors.

FIG. 5 depicts graphs of the variation of the R5/4 ratio parameter for test sensors stored for two weeks at 50° C., relative to the R5/4 ratio parameter for test sensors stored for two weeks at −20° C., where the test sensors had varying levels of enzyme density above the working electrode of the test sensors. The two types of data points represent the two different anionic surfactants Phospholan CS131 (nonylphenol ethoxylate phosphate) and Geropon TC-42.

At higher concentrations of enzyme, the difference between the R5/4 ratio parameters for test sensors stored at 50° C. and for test sensors stored at −20° C. was smaller. This trend was evident for both types of anionic surfactants used in the reagent compositions. Since the R5/4 ratio parameter can be used as a variable in an index function for correcting analyte measurements, a lower variation of the parameter due to environmental factors is desirable. Thus, the increased retention of enzyme activity provided by the less aggressive desiccants can provide an added benefit of decreasing the variability of correction factors.

The enzyme in the reagent compositions of the test sensors used in FIGS. 1 through 5 was the FAD-GDH enzyme. The observed effects of residual moisture during storage of test sensors are believed to apply to other substantially water-soluble enzyme systems, such as systems including alcohol dehydrogenase, lactate dehydrogenase, β-hydroxybutyrate dehydrogenase, glucose-6-phosphate dehydrogenase, glucose oxidase (GOx), glucose dehydrogenase, formaldehyde dehydrogenase, malate dehydrogenase, and/or 3-hydroxysteroid dehydrogenase.

Preferable enzyme systems are oxygen independent, thus not substantially oxidized by oxygen. One such oxygen independent enzyme family is glucose dehydrogenase (GDH). Using different co-enzymes or co-factors, GDH may be mediated in a different manner by different mediators. Depending on their association with GDH, a co-factor, such as flavin adenine dinucleotide (FAD), can be tightly held by the host enzyme, such as in the case of FAD-GDH; or a co-factor, such as Pyrroloquinolinequinone (PQQ), may be covalently linked to the host enzyme, such as with PQQ-GDH. The co-factor in each of these enzyme systems may either be permanently held by the host enzyme, or the co-enzyme and the apo-enzyme may be reconstituted before the enzyme system is added to the reagent fluid. The co-enzyme also may be independently added to the host enzyme moiety in the reagent fluid to assist in the catalytic function of the host enzyme, such as in the cases of nicotinamide adenine dinucleotide $NAD/NADH^+$ or nicotinamide adenine dinucleotide phosphate $NADP/NADPH^+$ in combination with NAD-dependent glucose dehydrogenase (NAD-GDH).

Ingredients of reagent compositions for test sensors, and of reagent fluids for forming the reagent compositions, are described, for example, in U.S. Patent Pub. 2009/0178936 to Zhu, entitled "Porous Particle Reagent Compositions, Devices, and Methods for Biosensors"; and in International Patent Application No. PCT/US2009/066963, filed Dec. 7, 2009, entitled "Low Total Salt Reagent Compositions And Systems For Biosensors", published as WO 2010/0077598. The disclosures of these patent applications regarding reagent composition ingredients and fluids for forming reagent compositions are herein incorporated by reference.

Both the enzyme activity in test sensors and the measurement performance of the test sensors appear to be affected by the type of desiccant used in the container for the sensors. A desiccant that adsorbs at most 15% of its weight in water, or that preferably adsorbs at most 10% or from 5%-10% of its weight in water, when in contact with an environment of 10%-20% RH at 40° C. may provide a residual moisture level in the regent composition that allows the enzyme to be retained in its active state, even in the absence of an enzyme stabilizer such as a sugar or a sugar alcohol. In contrast, excessive drying of the reagent composition by an aggressive desiccant, such as molecular sieve, may lead to enzyme inactivation. The less aggressive desiccants may balance the opposite moisture requirements for the mediator and the enzyme in containers for test sensors by adsorbing water from the atmosphere only when humidity level in the package exceeds 20% RH. Thus, the less aggressive desiccants may protect the mediator from high moisture without adversely affecting the enzyme activity.

The measurement performance of a test sensor may be increased by sealing the test sensor in a container including a desiccant that adsorbs at most 15% of its weight in water when in contact with an environment of 10%-20% RH at 40° C. For example, a test sensor that is sealed in a container including a desiccant that adsorbs at most 15% of its weight in water when in contact with an environment of 10%-20% RH at 40° C. may have increased measurement accuracy, as compared to a test sensor sealed in a container having no desiccant, or having a conventional desiccant such as molecular sieves. In another example, a test sensor that is sealed in a container including a desiccant that adsorbs at most 15% of its weight in water when in contact with an environment of 10%-20% RH at 40° C. may retain a higher percentage of activity of a redox enzyme in a reagent composition of the test sensor, as compared to a test sensor sealed in a container having no desiccant, or having a conventional desiccant such as molecular sieves. In another example, a plurality of test sensors that are sealed in a container including a desiccant that adsorbs at most 15% of its weight in water when in contact with an environment of 10%-20% RH at 40° C. may have increased measurement precision, as compared to a plurality of test sensors sealed in a container having no desiccant, or having a conventional desiccant such as molecular sieves.

Figure 6:
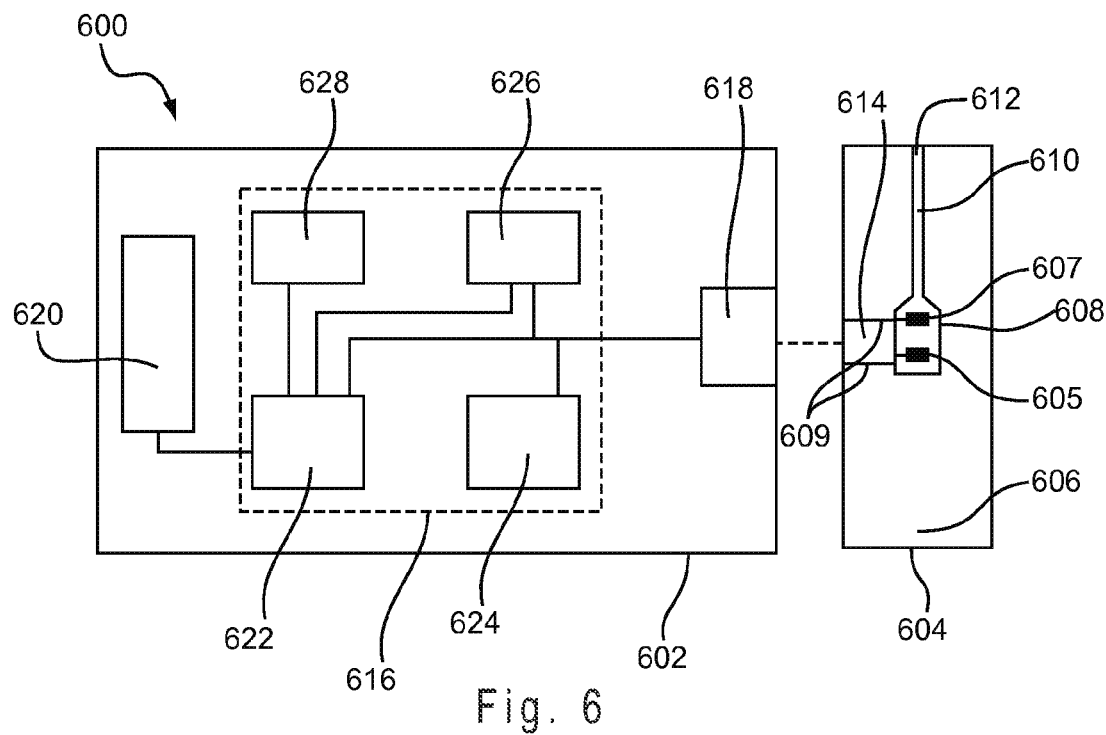
FIG. 6 depicts a schematic representation of a biosensor that determines an analyte concentration in a sample of a biological fluid using a test sensor.

FIG. 6 depicts a schematic representation of a biosensor 600 that determines an analyte concentration in a sample using a test sensor. The biosensor 600 may be utilized to determine one or more analyte concentrations such as alcohol, glucose, uric acid, lactate, cholesterol, bilirubin, free fatty acids, triglycerides, proteins, ketones, phenylalanine, enzymes or the like, in a biological fluid such as whole blood, urine, saliva or the like. While a particular configuration is shown, the biosensor 600 may have other configurations, including those with additional components.

The biosensor system 600 includes a measurement device 602 and a test sensor 604. The measurement device 602 may be implemented as a bench-top device, a portable or handheld device, or the like. A handheld device is a device that may be held in a human hand and is portable. An example of a handheld device is the measurement device of the Ascensia® Elite Blood Glucose Monitoring System, available from Bayer HealthCare, LLC, Elkhart, Ind. A desiccant that retains a residual moisture level in a container in which test sensors 604 are stored improves the accuracy and/or precision of the biosensor 600 in determining the concentration of the analyte in the sample.

The test sensor 604 has a base 606 forming a reservoir 608 with an opening 612. An optional channel 610 may provide fluid communication between the reservoir 608 and the opening 612. The reservoir 608 and the channel 610 may be covered by a lid with a vent (not shown). The reservoir 608 defines a partially-enclosed volume. The reservoir 608 may contain a composition that assists in retaining a liquid sample such as water-swellable polymers or porous polymer matrices. Reagents may be deposited in the reservoir 608 and/or channel 610. Reagents include one or more enzymes, mediators, binders, and other active or non-reactive species. The reagent composition at the working electrode 607 may include a low total salt reagent composition. The counter electrode 605 may be formed using the same or a different reagent composition, preferably one lacking an enzyme system. The test sensor 604 also may have a sample interface 614 in electrical communication with the partially-enclosed volume of the reservoir 608. The test sensor 604 may have other configurations.

The test sensor 604 is disposed adjacent to the measurement device 602. Adjacent includes positions where the sample interface 614 is in electrical communication with the sensor interface 618. Electrical communication includes wired or wireless transfer of input and/or output signals between contacts in the sensor interface 618 and conductors 609 in the sample interface 614.

The sample interface 614 has conductors 609 connected to the working electrode 607 and the counter electrode 605. The electrodes may be substantially in the same plane or in more than one plane. The electrodes 605, 607 may be disposed on a surface of the base 606 that forms the reservoir 608. The electrodes 605, 607 may extend or project into the reservoir 608. A dielectric layer may partially cover the conductors 609 and/or the electrodes 605, 607. A mediator may be disposed on or near the working and counter electrodes. The sample interface 614 may have other electrodes and conductors.

The measurement device 602 includes electrical circuitry 616 connected to a sensor interface 618 and a display 620. The electrical circuitry 616 includes a processor 622 connected to a signal generator 624, an optional temperature sensor 626, and a storage medium 628. Measurement device 602 may have other components and configurations.

The signal generator 624 provides electrical excitation signals to the sensor interface 618 in response to the processor 622. Electrical excitation signals may be transmitted by the sensor interface 618 to the sample interface 614 to apply the electrical excitation signals to the sample. Electrical excitation signals may be a potential or current and may be constant, variable, or a combination thereof, such as when an AC signal is applied with a DC signal offset. Electrical excitation signals may be applied as a single pulse or in multiple pulses, sequences, or cycles. The signal generator 624 also may record signals received from the sensor interface 618 as a generator-recorder.

The optional temperature sensor 626 determines a temperature for use during the analysis of the sample. The temperature of the sample may be directly measured, calculated from the output signal, or presumed to be the same or similar to a measurement of the ambient temperature or the temperature of the measurement device 602 implementing the biosensor 600. The temperature may be measured using a thermister, thermometer, infrared sensor, thermopile or other temperature sensing device. Other techniques may be used to determine the sample temperature.

The storage medium 628 may be a magnetic, optical, or semiconductor memory, another storage device, or the like. The storage medium 628 may be a fixed memory device, a removable memory device, such as a memory card, remotely accessed, or the like.

The processor 622 implements the analyte analysis and data treatment using processor readable software code and data stored in the storage medium 628. The processor 622 may start the analyte analysis in response to the presence of the test sensor 604 at the sensor interface 618, the application of a sample to the test sensor 604, user input, or the like. The processor 622 directs the signal generator 624 to provide the electrical input signal to the sensor interface 618.

The processor 622 receives and measures output signals from the sensor interface 618. Output signals may be electrical signals, such as current or potential. Output signals may include polling output signals such as those used in an underfill management system. Output signals include the analytic output signal generated in response to the redox reaction of the measurable species in the sample used to determine the analyte concentration of the sample. Processor 622 may compare the polling and/or analytic output signals to one or more thresholds.

The processor 622 preferably measures the output signal to obtain a current value from an excitation where the initial current value is greater than those that follow in the decay and within less than about 3 seconds of introducing the sample to the test sensor 604. More preferably, the processor 622 measures the output signal to obtain a current value within less than about 3 seconds of introducing the sample to the test sensor in 604 and obtains the first current value recorded from an excitation where the current values that follow the first current value continuously decrease. Even more preferably, the processor 622 measures the output signal to obtain a current value within less than about 3 seconds of introducing the sample to the test sensor in 604, to obtain the first current value recorded from an excitation where the current values that follow the first current value continuously decrease, and to obtain a current value during the maximum kinetic performance of the test sensor.

The processor 622 determines analyte concentrations from output signals using one or more correlation equations. The results of the analyte analysis may be output to the display 620 and may be stored in the storage medium 628. Preferably, the results of the analyte analysis are output to the display 620 within five seconds or less of introducing the sample to the test sensor, more preferably the results are output to the display 620 within three seconds or less of introducing the sample to the test sensor.

The correlation equations relating analyte concentrations and output current values may be represented graphically, mathematically, a combination thereof, or the like. The correlation equations may be represented by a program number (PNA) table, another look-up table, or the like that is stored in the storage medium 628. Instructions regarding implementation of the analyte analysis may be provided by the computer readable software code stored in the storage medium 628. The code may be object code or any other code describing or controlling the functionality described herein. The data from the analyte analysis may be subjected to one or more data treatments, including the determination of decay rates, K constants, ratios, and the like in the processor 622.

The sensor interface 618 has contacts that connect or electrically communicate with the conductors 609 in the sample interface 614 of the test sensor 604. Electrically communicate includes through wires, wirelessly, and the like. The sensor interface 618 transmits the electrical excitation signals from the signal generator 624 through the contacts to the conductors 609 in the sample interface 614. The sensor interface 618 also transmits the output signal from the sample interface 614 to the processor 622 and/or the signal generator 624.

The display 620 may be analog or digital. The display may be a LCD, LED, OLED, TFT, vacuum fluorescent or other display adapted to display a numerical reading. Other displays may be used. The display 620 electrically communicates with the processor 622. The display 620 may be separate from the measurement device 602, such as when in wireless communication with the processor 622. Alternatively, the display 620 may be removed from the measurement device 602, such as when the measurement device 602 electrically communicates with a remote computing device, medication dosing pump, and the like.

In use, the biosensor system 600 activates and performs one or more diagnostic routines or other preparation functions prior to an analysis of a sample. The sample interface 614 of the test sensor 604 is in electrical and/or optical communication with the sensor interface 618 of the measurement device 602. Electrical communication includes the transfer of input and/or output signals between contacts in the sensor interface 618 and conductors in the sample interface 614. The test sensor 604 receives a sample, preferably the liquid form of a biological fluid. The sample is transferred into the volume formed by the reservoir 608 by introducing the sample to the opening 612. The sample flows through the optional channel 610 into the reservoir 608, filling the volume while expelling the previously contained air. The sample chemically reacts with the reagents deposited in the channel 610 and/or reservoir 608. Preferably, the sample is a fluid, more preferably, a liquid.

Processor 622 preferably recognizes when a sample is present or not present for analysis. Sample interface 614 provides the sample output signal to the sensor interface 618. Processor 622 receives the sample output signal from the sensor interface 618. Processor 622 may show the sample output signal on the display 620 and/or may store the sample output signal in the storage medium 628. Processor 622 may detect that a sample is present when a sample polling output signal reaches one or more sample thresholds or when electrical conductivity occurs between two or more electrodes. Processor 622 may detect that a sample is not present when the sample polling output signal does not reach one or more sample thresholds or when electrical conductivity does not occur between two or more electrodes.

Figure 7:
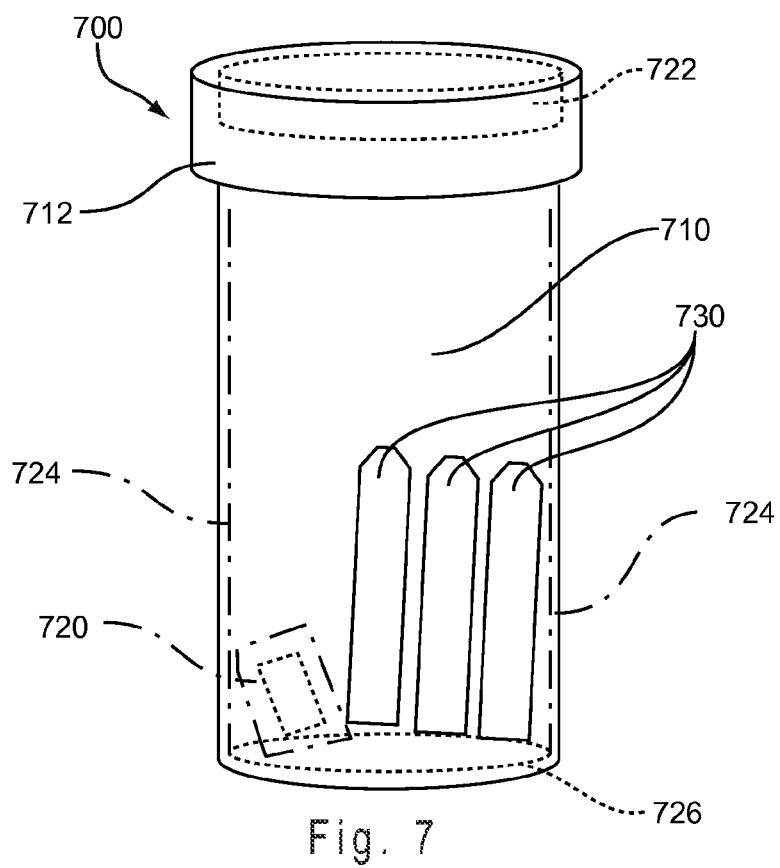
FIG. 7 depicts a sealed container containing a desiccant and a plurality of test sensors.

FIG. 7 depicts a biosensor system 700 that includes a container 710 including a desiccant and a plurality of test sensors 730. The container 710 includes a closure 712 that can seal the test sensors 730 in the container 710. The system 700 may include at least 5, at least 10, at least 25, at least 50, or at least 100 test sensors 730 sealed in the container 710. The container 710 may include desiccant 720 in a separate package in the container, such as a packet or disk containing the desiccant. The container 710 may include desiccant 722 in the closure 712. The container 710 may include desiccant 724 in a wall of the container, such as in a molded sleeve containing the desiccant. The container 710 may include desiccant 726 in the base of the container. The container 710 may be made of a variety of materials, including plastic, metal foil and/or glass. The amount and type of desiccant in the container 710 may be selected to provide a predetermined moisture level in the container.

Figure 8A:
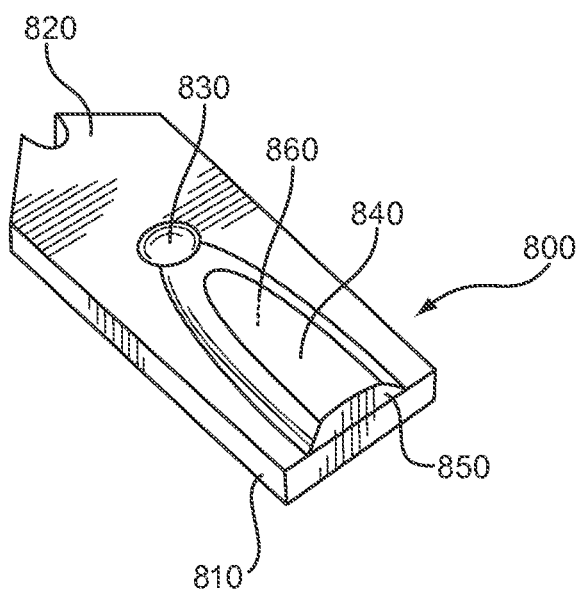
FIG. 8A is a perspective representation of an assembled test sensor.
Figure 8B:
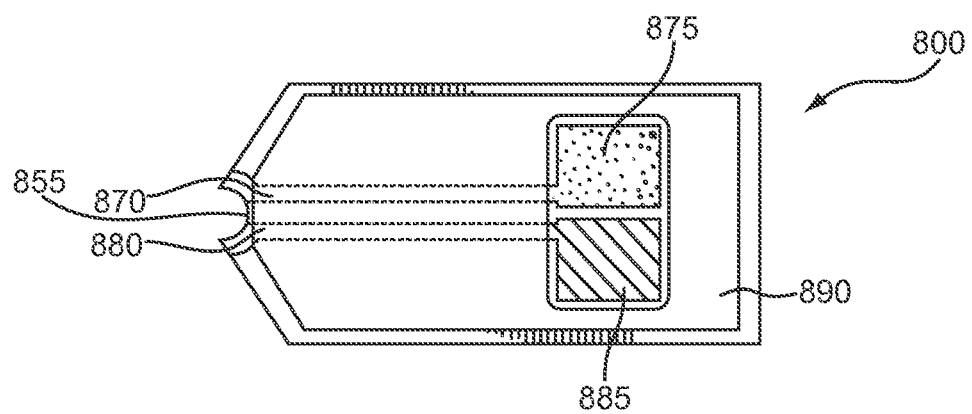
FIG. 8B is a top-view representation of the test sensor of FIG. 8A, with the lid removed.

FIGS. 8A and 8B depict a test sensor 800. FIG. 8A is a perspective representation of the assembled test sensor 800 including a sensor base 810 at least partially covered by a lid 820, and including a vent 830, a sample coverage area 840, and an input end opening 850. A partially-enclosed reservoir 860 is formed between the base 810 and the lid 820. Other test sensor designs also may be used.

A liquid sample for analysis may be transferred into the reservoir 860 by introducing the liquid to the opening 850. The liquid fills the reservoir 860 while expelling the previously contained air through the vent 830. The reservoir 860 may contain a retention composition (not shown) that assists in retaining the liquid sample in the reservoir. Examples of retention compositions include water-swellable polymers, such as carboxymethyl cellulose and polyethylene glycol; and porous polymer matrices, such as dextran and polyacrylamide.

FIG. 8B represents a top-view of the test sensor 800, with the lid 820 removed. Conductors 870 and 880 may run under a dielectric layer 890 from a measurement device interface 855 to a working electrode 875 and a counter electrode 885, respectively. The working and counter electrodes 875, 885 may be in substantially the same plane, as depicted in the figure, or in different planes (not shown). The working and counter electrodes 875, 885 may be separated from an upper portion of the lid 820 by at least 100 μm. The dielectric layer 890 may partially cover the electrodes 875, 885 and may be made from any suitable dielectric material, such as an insulating polymer.

The counter electrode 885 may support the electrochemical activity at the working electrode 875 of the test sensor 800. The potential to support the electrochemical activity at the working electrode 875 may be provided to the sensor system by forming the counter electrode 885 from an inert material, such as carbon, and including a soluble redox species, such as a ferricyanide mediator, within the reservoir 860. The potential at the counter electrode 885 may be a reference potential achieved by forming the counter electrode 885 from a redox pair, such as Ag/AgCl, to provide a combined reference-counter electrode. Alternatively, the test sensor 800 may be provided with a third conductor and electrode (not shown) to provide a reference potential to the sensor system. The area of the working electrode 875 may be the same as the area of the counter electrode 885, or one of the electrodes may have a larger area than the other electrode. Presently, it is preferred that the working electrode area is smaller than the counter electrode area.

Figure 9:
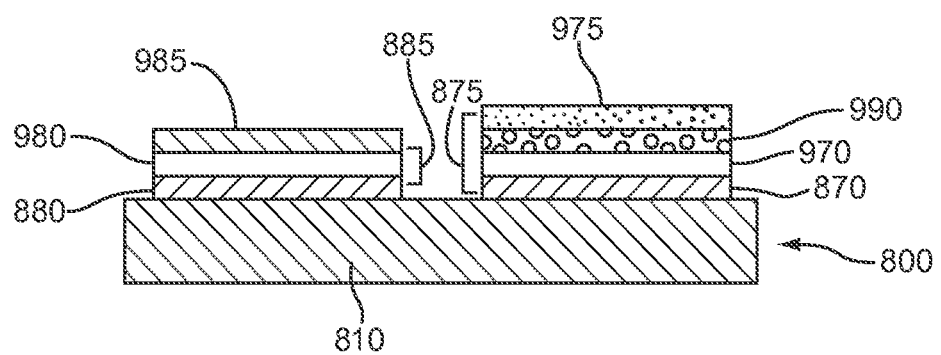
FIG. 9 is an end view representation of the test sensor of FIG. 8B.

FIG. 9 represents an end-view diagram of the test sensor of FIG. 8B showing the layer structures of the working electrode 875 and the counter electrode 885. The conductors 870 and 880 may be disposed directly on the base 810. Surface conductor layers 970 and 980 optionally may be disposed on the conductors 870 and 880, respectively. The surface conductor layers 970, 980 may be made from the same or from different materials as the conductors 870, 880.

The material or materials used to form the conductors 870, 880 and the surface conductor layers 970, 980 may include any electrical conductor. Preferable electrical conductors are non-ionizing, such that the material does not undergo a net oxidation or a net reduction during analysis of the sample. The conductors 870, 880 preferably include a thin layer of a metal paste or metal, such as gold, silver, platinum, palladium, copper, or tungsten. The surface conductor layers 970, 980 preferably include carbon, gold, platinum, palladium, or combinations thereof. If a surface conductor layer is not present on a conductor, the conductor is preferably made from a non-ionizing material.

The reagent compositions 975 and 985 may be disposed on or near the conductors 870 and 880, respectively. The term "on" is defined as "above" and is relative to the orientation being described. For example, if a first element is deposited over at least a portion of a second element, the first element is said to be "on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating may be described as "on" the first element. Thus, the use of the term "on" may or may not mean that the two elements being related are in physical contact.

The reagent compositions include reagents and a binder. The binder includes at least one polymeric material that is substantially water-soluble, and optionally may include substantially water-insoluble porous particles. The porous particles may provide additional physical structure to the polymeric material. Examples of porous particles for reagent compositions are disclosed, for example, in U.S. Patent Pub. 2009/0178936 A1, to Zhu, entitled "Porous Particle Reagent Compositions, Devices, and Methods for Biosensors". The binder may form a gel or gel-like material when hydrated by the sample. An optional layer 990 may be disposed on the conductor 870 and/or the surface conductor layer 970. The optional layer 990 may lack one or more constituents of the reagent composition 975.

The reagent compositions 975 and 985 may include the same or different reagents. When including the same reagents, the reagent compositions 975 and 985 may be the same composition. When including different reagents, the reagents present in the first composition 975 may be selected for use with the working electrode 875, while the reagents present in the second composition 985 may be selected for use with the counter electrode 885. For example, the reagents in the composition 985 may include a mediator to facilitate the free flow of electrons between the sample and the conductor 880. Similarly, the reagents in the composition 975 may include an enzyme system and optionally a mediator to facilitate the reaction of the analyte.

The enzyme system included in the reagent composition 975 may be specific to the analyte and may facilitate the reaction of the analyte while enhancing the specificity of the sensor system to the analyte, especially in complex biological samples. The enzyme system may include one or more enzyme, cofactor, and/or other moiety that participates in a redox reaction with the analyte. For example, an alcohol oxidase can be used to provide a test sensor that is sensitive to the presence of alcohol in a sample. Such a system could be useful in measuring blood alcohol concentrations. In another example, glucose dehydrogenase or glucose oxidase may be used to provide a test sensor that is sensitive to the presence of glucose in a sample. This system could be useful in measuring blood glucose concentrations, for example in patients known or suspected to have diabetes.

The ingredients of a reagent composition, such as 975, 985, may be quantified relative to the dimensions of the composition, or the ingredients may be quantified relative to another dimension of a sensor on which the composition is disposed, such as the reservoir volume or the working electrode area. In one example, an ingredient of a reagent composition may be quantified in terms of micrograms (μg), nanograms (ng), nanomoles (nmol), or enzyme units (U) per square millimeter ($mm^2$) of the reagent composition surface area, where the reagent composition surface area is the 2-dimensional area of the reagent composition. In another example, an ingredient of a reagent composition may be quantified in terms of micrograms (μg), nanomoles (nmol), or enzyme units (U) per microliter (μL) of the reservoir volume. In another example, an ingredient of a reagent composition may be quantified in terms of micrograms (μg), nanomoles (nmol), or enzyme units (U) per square millimeter ($mm^2$) of the working electrode area.

Suitable substantially water-soluble polymeric materials for use as the binder may include poly(ethylene oxide) (PEO), carboxymethyl cellulose (CMC), polyvinyl alcohol (PVA), hydroxyethyl cellulose (HEC), hydroxypropyl cellulose (HPC), ethyl hydroxyethyl cellulose, carboxymethyl ethyl cellulose, polyvinyl pyrrolidone (PVP), polyamino acids such as polylysine, polystyrene sulfonate, gelatin, acrylic acid, methacrylic acid, maleic anhydride salts thereof, derivatives thereof, and combinations thereof. Polymeric materials include monomers, pre-polymers, and other materials that form or have repeating units. Other polymeric materials may be used.

The reagent composition preferably includes from about 0.14 to about 0.43 μg of a binder per $mm^2$ of the reagent composition surface area, more preferably includes from about 0.17 to about 0.38 μg/$mm^2$ of a binder, and more preferably includes from about 0.22 to about 0.35 μg/$mm^2$ of a binder. The reagent composition preferably includes from about 1 to about 3 μg of a binder per μL of the reservoir volume, more preferably includes from about 1.2 to about 2.6 μg/μL of a binder, and more preferably includes from about 1.5 to about 2.3 μg/μL of a binder. The reagent composition preferably includes from about 1 to about 7.5 μg of a binder per $mm^2$ of the working electrode area, more preferably includes from about 1.2 to about 6.5 μg/$mm^2$ of a binder, and more preferably includes from about 1.5 to about 5.7 μg/$mm^2$ of a binder.

The reagent composition preferably includes a buffer salt. When the reagent composition is brought into contact with an aqueous sample, the buffer salt preferably maintains the pH of the mixture from about 4.5 to about 7.5, more preferably from about 6 to about 7. The preferred pH and buffer salt(s) for the reagent composition may be chosen to maintain the activity of the enzyme. Phosphate based buffers are presently preferred, but others may be used. Preferably the buffer salt includes $Na_2HPO_4$.

The reagent composition preferably includes from about 2.30 to about 9.54 nmol of a buffer salt per $mm^2$ of the reagent composition surface area, more preferably includes from about 2.80 to about 6.43 nmol/$mm^2$ of a buffer salt, and more preferably includes from about 3.40 to about 4.77 nmol/$mm^2$ of a buffer salt. The reagent composition preferably includes from about 16 to about 67 nmol of a buffer salt per μL of the reservoir volume, more preferably includes from about 20 to about 45 nmol/μL of a buffer salt, and more preferably includes from about 24 to about 34 nmol/μL of a buffer salt. The reagent composition preferably includes from about 16 to about 167 nmol of a buffer salt per $mm^2$ of the working electrode area, more preferably includes from about 20 to about 113 nmol/$mm^2$ of a buffer salt, and more preferably includes from about 24 to about 84 nmol/$mm^2$ of a buffer salt.

The reagent composition may include a one or two electron substantially water-soluble mediator. Mediators may be separated into two groups based on their electrochemical activity. One electron transfer mediators are chemical moieties capable of taking on one additional electron during the conditions of the electrochemical reaction, while two electron transfer mediators are chemical moieties capable of taking on two additional electrons during the conditions of the reaction. Examples of one electron transfer mediators include compounds, such as 1,1'-dimethyl ferrocene, ferrocyanide and ferricyanide, and ruthenium(III) and ruthenium(II) hexaamine. Examples of two electron transfer mediators include the organic quinones and hydroquinones, such as PIPT and PIPO as described above, and the carboxylic acid or salt, such as ammonium salts, of these phenothiazine derivatives, such as (E)-2-(3H-phenothiazine-3-ylideneamino)benzene-1,4-disulfonic acid, (E)-5-(3H-phenothiazine-3-ylideneamino)isophthalic acid, ammonium (E)-3-(3H-phenothiazine-3-ylideneamino)-5-carboxybenzoate, and combinations thereof. Examples of additional two electron transfer mediators include the electro-active organic molecules described in U.S. Pat. Nos. 5,393,615; 5,498,542; and 5,520,786.

The two electron transfer mediators listed above may include inorganic, non-transition metal salt as an impurity. The inorganic, non-transition metal salt typically is an alkali metal or alkaline earth metal salt of the sulfate ion, $[SO_4]^{2-}$. For example, (E)-2-(3H-phenothiazine-3-ylideneamino)benzene-1,4-disulfonic acid may include inorganic, non-transition metal salt as an impurity, with a mass percentage relative to the mediator from 1% (w/w) to 50% (w/w), such as from 3% (w/w) to 30% (w/w), from 4% (w/w) to 25% (w/w), and from 5% (w/w) to 21% (w/w).

The reagent composition preferably includes from about 1.70 to about 4.76 nmol of a mediator per $mm^2$ of the reagent composition surface area, more preferably includes from about 2.30 to about 5.14 $nmol/mm^2$ of a mediator, and more preferably includes from about 2.80 to about 4.00 $nmol/mm^2$ of a mediator. The reagent composition preferably includes from about 12 to about 40 nmol of a mediator per µL of the reservoir volume, more preferably includes from about 16 to about 36 nmol/µL of a mediator, and more preferably includes from about 20 to about 28 nmol/µL of a mediator. The reagent composition preferably includes from about 12 to about 100 nmol of a mediator per $mm^2$ of the working electrode area, more preferably includes from about 16 to about 90 $nmol/mm^2$ of a mediator, and more preferably includes from about 20 to about 70 $nmol/mm^2$ of a mediator. The reagent composition preferably includes at most 4.76 nmol of a mediator per $mm^2$ of the reagent composition surface area, at most 40 nmol of a mediator per µL of the reservoir volume, or at most 100 nmol of a mediator per $mm^2$ of the working electrode area.

The reagent composition also includes a substantially water-soluble enzyme system, such as a FAD-GDH system, as described above. The reagent composition preferably includes from about 0.07 to about 0.3 active unit (U, as specified by the manufacturer) of an enzyme system per $mm^2$ of the reagent composition surface area, more preferably includes from about 0.09 to about 0.25 $U/mm^2$ of an enzyme system, and more preferably includes from about 0.1 to about 0.2 $U/mm^2$ of an enzyme system. The reagent composition preferably includes from about 0.5 to about 1.8 U of an enzyme system per µL of the reservoir volume, more preferably includes from about 0.6 to about 1.6 U/µL of an enzyme system, and more preferably includes from about 0.8 to about 1.4 U/µL of an enzyme system. The reagent composition preferably includes from about 0.5 to about 5 U of an enzyme system per $mm^2$ of the working electrode area, more preferably includes from about 0.6 to about 4 $U/mm^2$ of an enzyme system, and more preferably includes from about 0.8 to about 3.5 $U/mm^2$ of an enzyme system.

The reagent composition preferably includes a non-ionic surfactant. The surfactant can be any non-ionic surfactant that assists in the formation of a colloidal suspension of the desired viscosity and stability and that is compatible with the deposition method and analysis. Examples of non-ionic surfactants include saccharide-based surfactants, such as N-heptanoyl-N-methylglucamine, N-octanoyl-N-methylglucamine, N-nonanoyl-N-methylglucamine, N-decanoyl-N-methylglucamine, octyl β-D-glucopyranoside, hexyl β-D-glucopyranoside, and n-heptyl β-D-glucopyranoside. At present, saccharide-based surfactants such as N-octanoyl-N-methyl-D-glucamine (sold as MEGA 8 and available from DOJINDO, Gaithersburg, Md.) and ethoxylate based neutral surfactants, such as the PEG-30 tetramethyl decynediol surfactants (SURFYNOL 485, for example, as available from Air Products, Allentown, Pa.) are preferred.

The reagent composition preferably includes from about 0.04 to about 0.24 µg of a non-ionic surfactant per $mm^2$ of the reagent composition surface area, more preferably includes from about 0.07 to about 0.21 $µg/mm^2$ of a non-ionic surfactant, and more preferably includes from about 0.09 to about 0.18 $µg/mm^2$ of a non-ionic surfactant. The reagent composition preferably includes from about 0.3 to about 1.7 µg of a non-ionic surfactant per µL of the reservoir volume, more preferably includes from about 0.5 to about 1.5 µg/µL of a non-ionic surfactant, and more preferably includes from about 0.6 to about 1.3 µg/µL of a non-ionic surfactant. The reagent composition preferably includes from about 0.3 to about 4.3 µg of a non-ionic surfactant per $mm^2$ of the working electrode area, more preferably includes from about 0.5 to about 3.8 $µg/mm^2$ of a non-ionic surfactant, and more preferably includes from about 0.6 to about 3.2 $µg/mm^2$ of a non-ionic surfactant.

The reagent composition optionally includes an anionic surfactant. The surfactant can be any anionic surfactant that assists in the formation of a well defined perimeter of the reagent composition and that is compatible with the deposition method and analysis. Examples of anionic surfactants include phosphate esters, such as alkylphenol ethoxylate phosphates; sulfates, such as alkylphenol ethoxylate sulfates; and sulfonates, such as alkyl and heteroalkyl sulfonates. Specific examples of anionic surfactants include the nonylphenol ethoxylate phosphates Phospholan CS131 and Phospholan CS141, sodium nonylphenol ethoxylate sulfate (Witcolate D-51-53), sodium methyl cocoyl taurate (Geropon TC-42) and sodium dioctyl sulfosuccinate.

The reagent composition preferably includes from about 3 to 16 nanograms (ng) of an anionic surfactant per $mm^2$ of the reagent composition surface area, more preferably includes from 4 to 12 $ng/mm^2$ of an anionic surfactant, and more preferably includes from 5.5 to 9 $ng/mm^2$ of an anionic surfactant. The reagent composition preferably includes from about 20 to 140 ng of an anionic surfactant per µL of the reservoir volume, more preferably includes from 30 to 80 ng/µL of an anionic surfactant, and more preferably includes from 35 to 60 ng/µL of an anionic surfactant. The reagent composition preferably includes from about 10 to 350 ng of an anionic surfactant per $mm^2$ of the working electrode area, more preferably includes from 30 to 220 $ng/mm^2$ of an anionic surfactant, and more preferably includes from 40 to 150 $ng/mm^2$ of an anionic surfactant.

The reagent composition preferably is a low total salt reagent composition, which has a lower concentration of buffer salt and/or a lower concentration of other salts than a conventional reagent composition. Preferably the low total salt reagent composition includes at most 9.54 nmol of a buffer salt per $mm^2$ of the reagent composition surface area, and at most 20% (w/w) inorganic, non-transition metal salt in the mediator. More preferably the low total salt reagent composition includes at most 6.43 nmol of a buffer salt per $mm^2$ of the reagent composition surface area, and at most 10% (w/w) inorganic, non-transition metal salt in the mediator. More preferably the low total salt reagent composition includes at most 4.77 nmol of a buffer salt per $mm^2$ of the reagent composition surface area, and at most 5% (w/w) inorganic, non-transition metal salt in the mediator.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A biosensor system, for determining the concentration of an analyte in a sample, comprising:
    a plurality of test sensors, each test sensor comprising
        at least two conductors, where one of the conductors is a working electrode, and
        a reagent composition disposed on or near the working electrode; and
    a container comprising a desiccant and the plurality of test sensors, sealed in the container, where the desiccant adsorbs at most 15% of its weight in water when in contact with an environment of 10%-20% RH at 40° C., the desiccant comprising a blend of molecular sieves and silica gel, the container comprising the desiccant retaining an appropriate residual moisture level;

where the appropriate residual moisture level in the container is such that, when the container is stored for two weeks at a temperature of 50° C., and each test sensor is subsequently removed from the container, connected through the at least two conductors to a measurement device and then contacted with one of a plurality of samples including an analyte, and the analyte concentration in each sample is determined by the test sensor and the measuring device, the plurality of samples having analyte concentrations that span the range of 50 mg/dL-600 mg/dL, the bias of each determined analyte concentration less than 100 mg/dL is within ±10 mg/dL, and the bias of each determined analyte concentration of at least 100 mg/dL is within ±10%.

2. The biosensor system of claim 1, where the bias of each determined analyte concentration less than 100 mg/dL is within ±7 mg/dL, and the bias of each determined analyte concentration of at least 100 mg/dL is within ±7%.

3. The biosensor system of claim 1, where the bias of each determined analyte concentration less than 100 mg/dL is within ±5 mg/dL, and the bias of each determined analyte concentration of at least 100 mg/dL is within ±5%.

4. The biosensor system of claim 1, where the desiccant adsorbs at most 10% of its weight in water when in contact with an environment of 10%-20% RH at 40° C.

5. The biosensor system of claim 1, where the desiccant adsorbs from 5%-10% of its weight in water when in contact with an environment of 10%-20% RH at 40° C.

6. The biosensor system of claim 1, where the container comprises at most 10 mg of the silica gel per test sensor.

7. The biosensor system of claim 1, where the plurality of test sensors comprises at least 50 test sensors.

8. The biosensor system of claim 1, where the plurality of test sensors comprises at least 100 test sensors.

9. The biosensor system of claim 1, wherein the coefficient of variation of the determined analyte concentrations is at most 2.5%.

10. A biosensor system, for determining the concentration of an analyte in a sample, comprising:
a plurality of test sensors, each test sensor comprising
at least two conductors, where one of the conductors is a working electrode, and
a reagent composition disposed on or near the working electrode, the reagent composition comprising a redox enzyme having an activity; and
a container comprising 7.5 to 30 mg per test sensor of a desiccant and the plurality of test sensors, sealed in the container, the desiccant including
a pure molecular sieve desiccant or a polymer-blended molecular sieve, and
silica gel or a polypropylene film coated with silica gel;
where, when the container is stored for two weeks at a temperature of 50° C., and each test sensor is subsequently removed from the container, the reagent composition of each test sensor retains at least 75% of the activity of the redox enzyme.

11. The biosensor system of claim 10, where the reagent composition of each test sensor retains at least 80% of the activity of the redox enzyme.

12. A biosensor system, for determining the concentration of an analyte in a sample, comprising:
a plurality of test sensors, each test sensor comprising
at least two conductors, where one of the conductors is a working electrode, and
a reagent composition disposed on or near the working electrode; and
a container comprising a desiccant and the plurality of test sensors, sealed in the container, the desiccant including a molecular sieve desiccant and silica gel;
where, when the container is stored for two weeks at a temperature of 50° C., and each test sensor is subsequently removed from the container, connected through the at least two conductors to a measurement device and then contacted with one of a plurality of samples including an analyte, and the analyte concentration in each sample is determined by the test sensor and the measuring device, the plurality of samples having analyte concentrations that span the range of 100 mg/dL-600 mg/dL, the coefficient of variation of the determined analyte concentrations is at most 2.5%.

13. The biosensor system of claim 12, wherein the desiccant includes about 22.5 mg per test sensor of molecular sieve desiccant.

14. The biosensor system of claim 12, wherein the desiccant includes about 30.0 mg per test sensor of silica gel.

15. A method of increasing the measurement performance of a test sensor, comprising:
sealing the test sensor in a container comprising a desiccant, the desiccant comprising
silica gel and polymer-blended molecular sieves, or
a blend of molecular sieves and silica gel;
the test sensor comprising at least two conductors, one of which is a working electrode, and a reagent composition disposed on or near the working electrode;
where the desiccant adsorbs at most 15% of its weight in water when in contact with an environment of 10%-20% RH at 40° C.

16. The method of claim 15, wherein the desiccant includes about 5 to about 30 mg of silica gel per test sensor.

17. A biosensor system, for determining the concentration of an analyte in a sample, comprising:
a plurality of test sensors, each test sensor comprising
at least two conductors, where one of the conductors is a working electrode, and
a reagent composition disposed on or near the working electrode; and
a container comprising a desiccant and the plurality of test sensors, sealed in the container, the desiccant comprising silica gel and polymer-blended molecular sieves, or a blend of molecular sieves and silica gel;
where the desiccant adsorbs at most 15% of its weight in water when in contact with an environment of 10%-20% RH at 40° C.

18. The biosensor system of claim 17, where the desiccant includes at most 10 mg of the silica gel per test sensor.

19. A biosensor system, for determining the concentration of an analyte in a sample, comprising:
a plurality of test sensors, each test sensor comprising
at least two conductors, where one of the conductors is a working electrode, and
a reagent composition, disposed on or near the working electrode, where the reagent composition comprises a redox enzyme having an activity, and is substantially free of a sugar or a sugar alcohol; and
a container comprising 7.5 to 30 mg per test sensor of a desiccant and the plurality of test sensors, sealed in the container, the desiccant including a pure molecular sieve desiccant or a polypropylene film coated with molecular sieves, and silica gel or a polypropylene film coated with silica gel;

where, when the container is stored for two weeks at a temperature of 50° C., and each test sensor is subsequently removed from the container, the reagent composition of each test sensor retains at least 75% of the activity of the redox enzyme.

20. A biosensor system for determining the concentration of an analyte in a sample, comprising:

a plurality of test sensors, each test sensor comprising
at least two conductors, one of the conductors being a working electrode, and
a reagent composition disposed on or near the working electrode; and a container comprising desiccant and the plurality of test sensors sealed in the container, the desiccant comprising up to 22.5 mg per test sensor molecular sieves and up to 30 mg per test sensor silica gel, the container comprising the desiccant retaining an appropriate residual moisture level;

where the appropriate residual moisture level in the container is such that, when the container is stored for two weeks at a temperature of 50° C., the bias of an analyte concentration determined using one of the plurality of test sensors less than 100 mg/dL is within ±10 mg/dL, and the bias of each determined analyte concentration of 100-600 mg/dL is within ±10%.

* * * * *